(12) United States Patent
Okada et al.

(10) Patent No.: US 11,942,213 B2
(45) Date of Patent: Mar. 26, 2024

(54) ENDOSCOPE SYSTEM, MEDICAL IMAGE PROCESSING DEVICE, AND OPERATION METHOD THEREFOR

(71) Applicant: FUJIFILM Corporation, Tokyo (JP)

(72) Inventors: Takahisa Okada, Kanagawa (JP); Haruo Akiba, Kanagawa (JP); Tetsuya Fujikura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/749,712

(22) Filed: May 20, 2022

(65) Prior Publication Data
US 2022/0375577 A1 Nov. 24, 2022

(30) Foreign Application Priority Data

May 24, 2021 (JP) .................................. 2021-087129

(51) Int. Cl.
| | | |
|---|---|---|
| G16H 30/40 | (2018.01) | |
| A61B 1/00 | (2006.01) | |
| A61B 1/045 | (2006.01) | |
| A61B 1/05 | (2006.01) | |
| G06T 7/00 | (2017.01) | |

(52) U.S. Cl.
CPC ....... *G16H 30/40* (2018.01); *A61B 1/000094* (2022.02); *A61B 1/000096* (2022.02); *A61B 1/045* (2013.01); *A61B 1/05* (2013.01); *G06T 7/0012* (2013.01); *G06T 2207/10068* (2013.01)

(58) Field of Classification Search
CPC .......... A61B 1/00009; A61B 1/000094; A61B 1/000096; A61B 1/00045; A61B 1/0005; A61B 1/00089; A61B 1/045; G06T 2207/10068; G06T 2207/30004; G06T 2207/30096

See application file for complete search history.

(56) References Cited

U.S. PATENT DOCUMENTS

| | | | |
|---|---|---|---|
| 2015/0031990 A1* | 1/2015 | Boctor | A61B 8/483 600/440 |
| 2017/0053090 A1* | 2/2017 | Viswanath | G06V 10/449 |

(Continued)

FOREIGN PATENT DOCUMENTS

| | | |
|---|---|---|
| JP | 2021-003453 A | 1/2021 |
| WO | 2020/023740 A1 | 1/2020 |

(Continued)

OTHER PUBLICATIONS

The extended European search report issued by the European Patent Office dated Oct. 18, 2022, which corresponds to European Patent Application No. 22175143.1-1126 and is related to U.S. Appl. No. 17/749,712.

*Primary Examiner* — John P Leubecker
(74) *Attorney, Agent, or Firm* — Studebaker & Brackett PC

(57) ABSTRACT

A medical image processing device includes a processor, in which the processor acquires an examination image of a subject captured by an endoscope, and identifies an incision suitable site in the subject included in the examination image and performs control for outputting incision suitable site information regarding the incision suitable site on the basis of the examination image, and the identification of the incision suitable site information is performed by using a learning image associated with a position of a muscular layer in the subject.

18 Claims, 15 Drawing Sheets

(56) References Cited

U.S. PATENT DOCUMENTS

| | | | |
|---|---|---|---|
| 2020/0273577 A1 | 8/2020 | Wolf et al. | |
| 2020/0297422 A1* | 9/2020 | Gocho | A61B 34/25 |
| 2021/0015554 A1 | 1/2021 | Chow et al. | |
| 2021/0088772 A1* | 3/2021 | Morita | G02B 23/2461 |
| 2021/0385367 A1* | 12/2021 | Yabe | A61B 1/0655 |
| 2021/0401268 A1* | 12/2021 | Takahashi | A61B 1/00045 |
| 2022/0301159 A1* | 9/2022 | Byun | G06T 7/70 |

FOREIGN PATENT DOCUMENTS

| | | |
|---|---|---|
| WO | 2020/174572 A1 | 9/2020 |
| WO | 2020/261648 A1 | 12/2020 |
| WO | 2022/051362 A1 | 3/2022 |

\* cited by examiner

ENDOSCOPE SYSTEM, MEDICAL IMAGE PROCESSING DEVICE, AND OPERATION METHOD THEREFOR

CROSS-REFERENCE TO RELATED APPLICATIONS

This application claims priority under 35 U.S.C § 119(a) to Japanese Patent Application No. 2021-087129 filed on 24 May 2021. The above application is hereby expressly incorporated by reference, in its entirety, into the present application.

BACKGROUND OF THE INVENTION

1. Field of the Invention

The present invention relates to an endoscope system, a medical image processing device, and an operation method therefor capable of supporting an operation such as endoscopic submucosal dissection.

2. Description of the Related Art

Endoscopic submucosal dissection (ESD) makes it possible to resect tumors or the like with a size to which endoscopic mucosal resection (EMR) cannot be applied and thus to complete an operation without selecting a highly invasive surgery. ESD is performed endoscopically, and thus has the advantage of being minimally invasive. On the other hand, there is also a demerit with the risk of perforation that a doctor erroneously punctures an organ.

There is a technique in which, in order to prevent perforation, from an endoscopic image acquired during examination, a situation is determined to be "dangerous" in a case where there is a possibility of perforation of a muscular layer being cut, and "safe" in other cases, and in the case of "dangerous", a signal is transmitted to an electric scalpel device to stop an output of the electric scalpel device (JP2021-3453A).

SUMMARY OF THE INVENTION

ESD goes through processes such as marking around a tumor, local injection into the submucosal layer, incision of the mucous membrane, peeling of the submucosal layer, and hemostasis. Since ESD requires advanced techniques such as not causing perforation and appropriately removing a lesion part, a technique for supporting an operator who is unfamiliar with surgery is required.

The present invention provides an endoscope system, a medical image processing device, and an operation method therefor capable of identifying and outputting a site of a subject that can be safely incised.

According to an aspect of the present invention, there is provided a medical image processing device including a processor, in which the processor acquires an examination image of a subject captured by an endoscope, and identifies an incision suitable site in the subject included in the examination image and performs control for outputting incision suitable site information regarding the incision suitable site on the basis of the examination image, and the identification of the incision suitable site information is performed by using a learning image associated with a position of a muscular layer in the subject.

It is preferable that the processor identifies an incision unsuitable site in the subject included in the examination image, and performs control for outputting incision unsuitable site information regarding the incision unsuitable site, and the identification of the incision unsuitable site information is performed by using the learning image associated with a position of fibrosis in the subject.

It is preferable that the processor identifies the incision suitable site and the incision unsuitable site by a suitability, and performs control for outputting the incision suitable site information as the suitability. A learning model is preferably generated by using the learning image.

The learning image preferably includes the subject into which a local injection solution is locally injected. The local injection solution preferably contains a staining solution. It is preferable that the staining solution is indigo carmine and the staining solution is indigo carmine, and the learning image is associated with a concentration of the indigo carmine.

The learning image is preferably associated with presence or absence of a cautery scar and/or coagulated blood in the subject.

The learning image is preferably associated with a position of a hood attached to a tip of the endoscope in the subject.

The learning image is preferably associated with a distance from a submucosal layer to the muscular layer and/or a distance from the submucosal layer to a lesion part in the subject.

It is preferable that, on the basis of the incision suitable site information, the processor generates a first display image indicating the incision suitable site as an image, and performs control for superimposing the first display image on the examination image to be displayed on the display.

The first display image preferably indicates the incision suitable site with a color, a symbol, or a figure. The figure is preferably a line.

The processor preferably performs control for displaying the distance from the submucosal layer to the muscular layer on the first display image.

It is preferable that, on the basis of the incision unsuitable site information, the processor generates a second display image indicating the incision unsuitable site as an image, and performs control for superimposing the second display image on the examination image to be displayed on a display.

It is preferable that the processor generates a perforation risk image indicating the suitability as an image, and performs control for superimposing the perforation risk image on the examination image to be displayed on a display.

It is preferable that, in a case where the examination image includes the incision unsuitable site, the processor performs control for providing a notification with sound or notification display.

It is preferable that, on the basis of the incision suitable site information, the processor generates incision support information corresponding to the incision suitable site information, and performs control for superimposing the incision support information on the examination image to be displayed on a display.

According to another aspect of the present invention, there is provided an operation method for a medical image processing device, including a step of acquiring an examination image of a subject captured by an endoscope; and a step of identifying an incision suitable site in the subject included in the examination image and performing control for outputting incision suitable site information regarding the incision suitable site, in which the identification of the incision suitable site information is performed by using a learning image associated with a position of a muscular layer in the subject.

According to still aspect of the present invention, there is provided an endoscope system including the medical image processing device and the endoscope.

According to the present invention, it is possible to provide an endoscope system, a medical image processing device, and an operation method therefor capable of identifying and outputting a site of a subject that can be safely incised.

DESCRIPTION OF THE PREFERRED EMBODIMENTS

Figure 1:
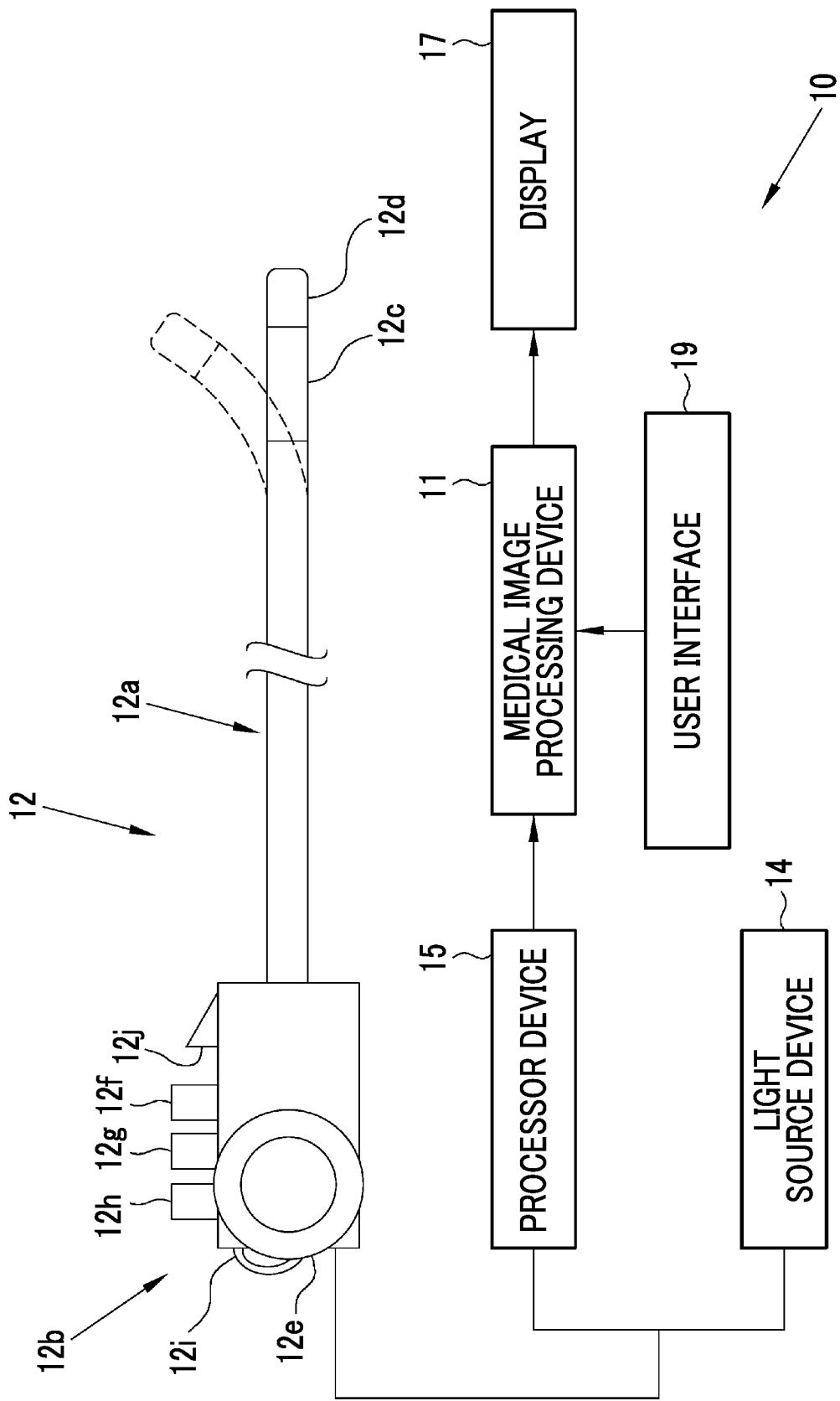
FIG. 1 is an explanatory diagram of a configuration of an endoscope system.

As shown in FIG. 1, a medical image processing device 11 is connected to an endoscope system 10 via a processor device 15. The endoscope system 10 includes an endoscope 12, a light source device 14, a processor device 15, a medical image processing device 11, a display 17, and a user interface 19. The endoscope 12 is optically connected to the light source device 14 and electrically connected to the processor device 15. The endoscope 12 is provided on an insertion part 12a to be inserted into the body of an observation target, an operating part 12b provided at a base end portion of the insertion part 12a, and a bending part 12c and a tip part 12d provided at a distal end side of the insertion part 12a. The bending part 12c is bent by operating an angle knob 12e of the operating part 12b. The tip part 12d is directed in a desired direction when the bending portion 12c is bent. A forceps channel (not shown) for inserting a treatment tool or the like is provided from the insertion part 12a to the tip part 12d. The treatment tool is inserted into the forceps channel from a forceps port 12j.

Inside the endoscope 12, an optical system for forming a subject image and an optical system for irradiating the subject with illumination light are provided. The operating part 12b is provided with an angle knob 12e, an observation mode selector switch 12f, an image analysis mode selector switch 12g, a still image acquisition instruction switch 12h, and a zoom operating part 12i. The observation mode selector switch 12f is used for an observation mode selection operation. The still image acquisition instruction switch 12h is used for an instruction for acquiring a still image of an observation target. The zoom operating part 12i is used to operate the zoom lens 42.

The light source device 14 generates illumination light. The display 17 outputs and displays an examination image and an image in which incision suitable site information and/or incision unsuitable site information that will be described later is superimposed on the examination image. The user interface 19 has a keyboard, a mouse, a touch pad, a microphone, and the like, and has a function of receiving input operations such as function settings. The processor device 15 performs system control on the endoscope system 10 and image processing and the like on an image signal transmitted from the endoscope 12.

Figure 2:
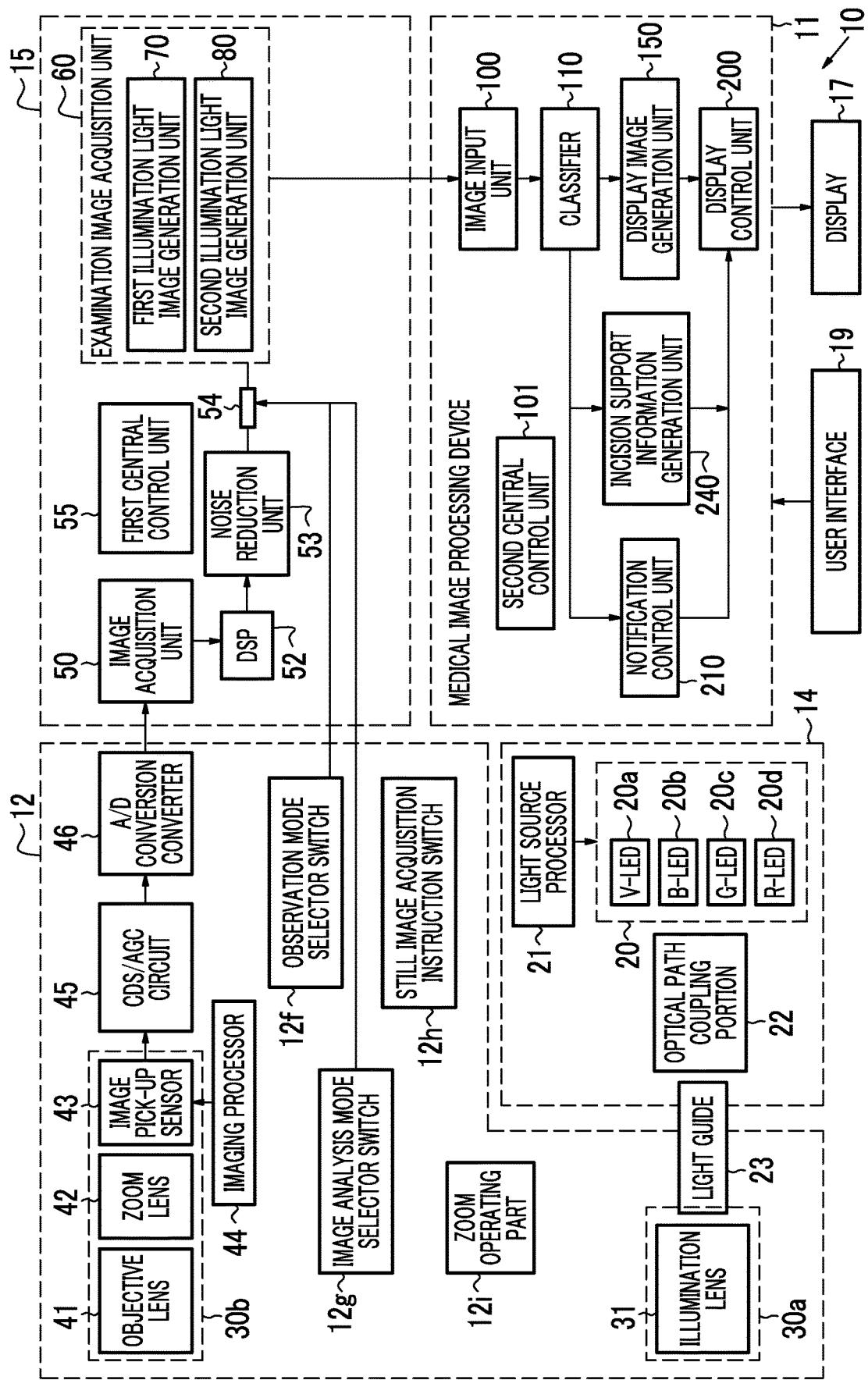
FIG. 2 is a block diagram showing a function of the endoscope system.

In FIG. 2, the light source device 14 includes a light source unit 20 and a light source processor 21 that controls the light source unit 20. The light source unit 20 has, for example, a plurality of semiconductor light sources, each of which is turned on or off, and in a case where the light source unit 20 is turned on, a light emission amount of each semiconductor light source is controlled such that illumination light for illuminating an observation target is emitted. The light source unit 20 includes four color LEDs such as a violet light emitting diode (V-LED) 20a, a blue light emitting diode (B-LED) 20b, and a green light emitting diode (G-LED) 20c, and a red light emitting diode (R-LED) 20d. The light source unit 20 may be built in the endoscope 12, and the light source control unit may be built in the endoscope 12, or may be built in the processor device 15.

Figure 3:
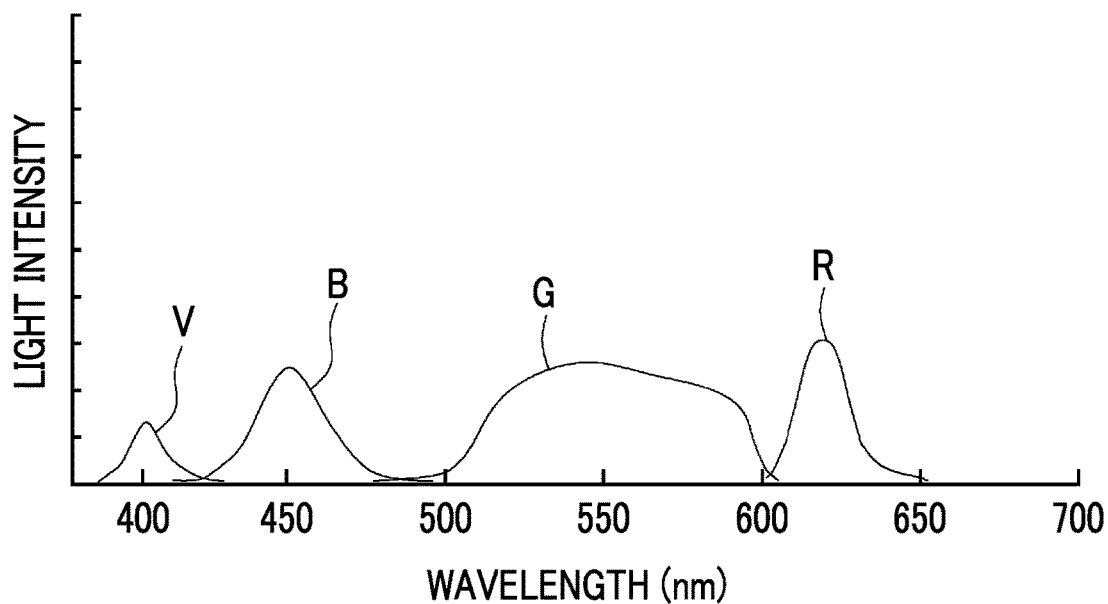
FIG. 3 is a graph showing spectra of violet light V, blue light B, green light G, and red light R.

As shown in FIG. 3, the V-LED 20a generates violet light V having a central wavelength of 405±10 nm and a wavelength range of 380 to 420 nm. The B-LED 20b generates blue light B having a central wavelength of 450±10 nm and a wavelength range of 420 to 500 nm. The G-LED 20c generates green light G having a wavelength range of 480 to 600 nm. The R-LED 20d generates red light R having a central wavelength of 620 to 630 nm and a wavelength range of 600 to 650 nm.

The endoscope system 10 has, as observation modes, three modes such as a first illumination observation mode, a second illumination observation mode, and an image analysis mode. In a case where the observation mode selector switch 12f is pressed, the modes are switched via an image processing switching unit 54 (refer to FIG. 2).

In the first illumination observation mode, a first illumination light image having a natural color is displayed on the display 17 by causing normal light such as white light (first illumination light) to illuminate an observation target and picking up an image thereof. In the second illumination observation mode, a second illumination light image emphasizing a specific structure is displayed on the display 17 by causing special light (second illumination light) having a wavelength band different from that of the normal light to illuminate an observation target and pick up an image thereof. The first illumination light image and the second illumination light image are a kind of examination image.

Light used for performing ESD is usually the first illumination light. In a case where it is desired to check an infiltration range of a lesion part before performing ESD, the second illumination light may be used. A learning image used for learning of a classifier 110 (refer to FIG. 2) that will be described later is preferably the first illumination light image. The second illumination light image in which a lesion part is particularly emphasized may be associated with various types of information, and may be used as a learning image. Examination images and learning images are a kind of medical image.

The light source processor 21 controls the V-LED 20a, the B-LED 20b, the G-LED 20c, and the R-LED 20d. By independently controlling each of the LEDs 20a to 20d, the light source processor 21 can emit the violet light V, the blue light B, the green light G, or the red light R by independently changing an amount of light. In the first illumination observation mode, the light source processor 21 controls the respective LEDs 20a to 20d such that white light in which a light amount ratio between the violet light V, the blue light B, the green light G, and the red light R is Vc:Bc:Gc:Rc is emitted. Here, Vc, Bc, Gc, and Rc>0.

In the second illumination observation mode, the light source processor 21 controls the respective LEDs 20a to 20d such that special light in which a light amount ratio between the violet light V as short-wavelength narrow-band light, the blue light B, the green light G, and the red light R is Vs:Bs:Gs:Rs is emitted. The light amount ratio Vs:Bs:Gs:Rs is different from the light amount ratio Vc:Bc:Gc:Rc used in the first illumination observation mode, and is set as appropriate according to observation purposes.

Figure 4:
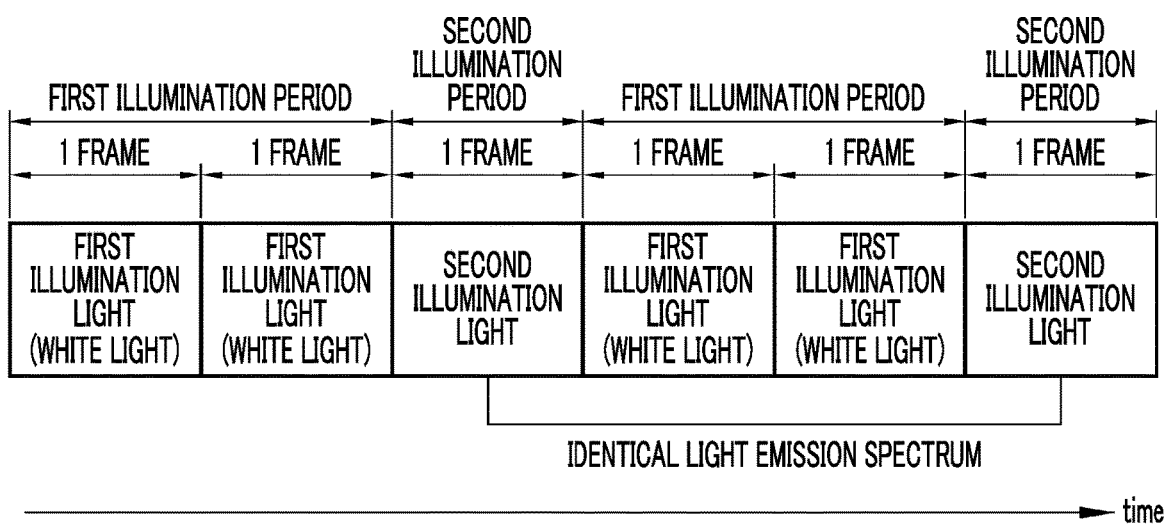
FIG. 4 is an explanatory diagram showing a first light emission pattern in an image analysis mode.
Figure 5:
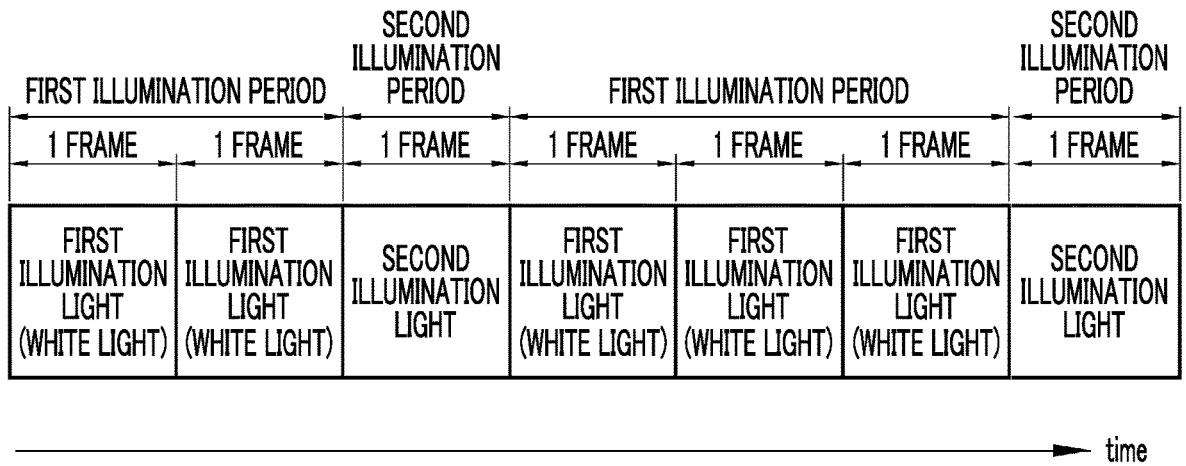
FIG. 5 is an explanatory diagram showing a second light emission pattern in the image analysis mode.

In the image analysis mode, the light source processor 21 switches between the first illumination light and the second illumination light having different emission spectra to emit light. Specifically, the first illumination light and the second illumination light are switched therebetween, as a light emission pattern, as shown in FIG. 4, as in a first light emission pattern in which the number of frames in a first illumination period is the same as that in each first illumination period and, as shown in FIG. 5, a second light emission pattern in which the number of frames in the first illumination period is different from that in each first illumination period. In the figures, time represents a direction of passage of time.

In a case of performing ESD, the first illumination light image and the second illumination light image may be obtained by automatically switching between the first illumination light and the second illumination light, and positions of lesion parts, muscular layers, submucosal layers, and the like are aligned and associated with each other between the first illumination light image in which an operational field is visible in a natural color and the second illumination light image in which the lesion part is emphasized, and the images may be used as learning images for learning of the classifier 110. By using the learning image in which the positions of the lesion parts, the muscular layers, the submucosal layers, and the like are associated with each other between the first illumination light image and the second illumination light image, it is possible to generate a learning model that can identify a distance from the submucosal layer to the lesion part more finely.

The light emitted by each of the LEDs 20a to 20d (refer to FIG. 2) is incident to a light guide 23 via an optical path coupling portion 22 configured with a mirror, a lens, and the like. The light guide 23 propagates light from the optical path coupling portion 22 to the tip part 12d of the endoscope 12.

An illumination optical system 30a and an image pick-up optical system 30b are provided at the tip part 12d of the endoscope 12. The illumination optical system 30a has an illumination lens 31, and the illumination light propagated by the light guide 23 is applied to an observation target via the illumination lens 31. In a case where the light source unit 20 is built in the tip part 12d of the endoscope 12, the light source unit 20 emits light toward a subject via the illumination lens of the illumination optical system without using the light guide. The image pick-up optical system 30b has an objective lens 41 and an image pick-up sensor 43. Light from an observation target due to the irradiation of the illumination light is incident to the image pick-up sensor 43 via the objective lens 41 and the zoom lens 42. Consequently, an image of the observation target is formed on the image pick-up sensor 43. The zoom lens 42 is a lens for enlarging the observation target, and is moved between the telephoto end and the wide-angle end by operating the zoom operating part 12i.

Figure 6:
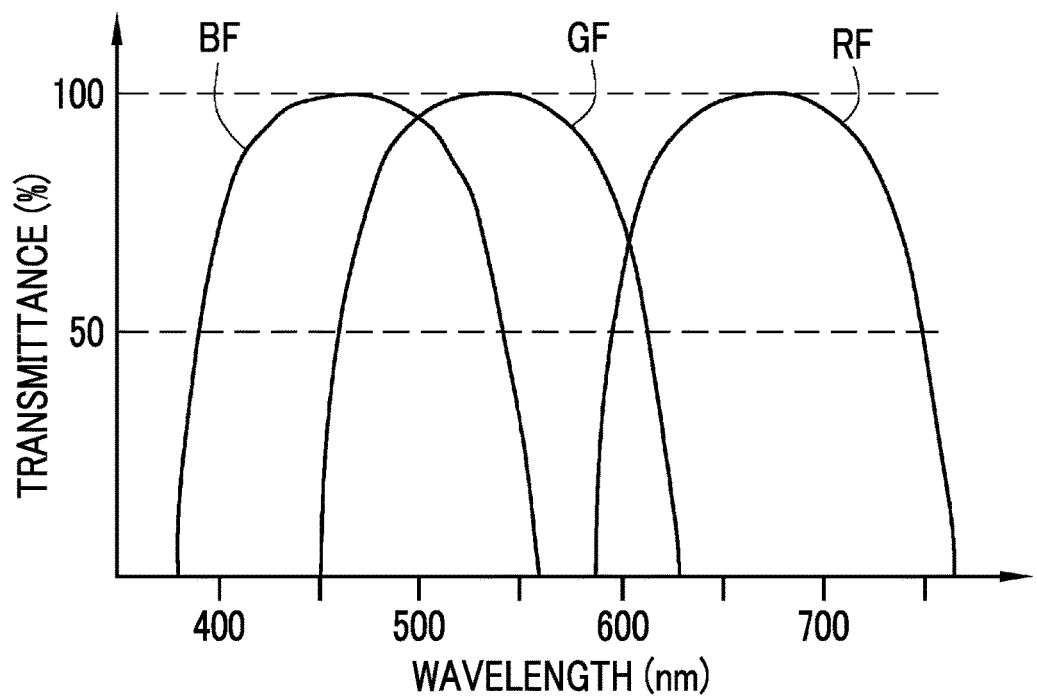
FIG. 6 is a graph showing the spectroscopic transmittance of each color filter of an image pick-up sensor.

The image pick-up sensor 43 is a primary color sensor, and includes three types of pixels such as a blue pixel (B pixel) having a blue color filter, a green pixel (G pixel) having a green color filter, and a red pixel (R pixel) having a red color filter. As shown in FIG. 6, a blue color filter BF mainly transmits light in the blue band, specifically, light in the wavelength band of 380 to 560 nm. The transmittance of the blue color filter BF peaks in the vicinity of the wavelength of 460 to 470 nm. The green color filter GF mainly transmits light in the green band, specifically, light in the wavelength band of 460 to 620 nm. The red color filter RF mainly transmits light in the red band, specifically, light in the wavelength band of 580 to 760 nm.

The image sensor 43 is preferably a charge-coupled device (CCD) or a complementary metal oxide semiconductor (CMOS). The image pick-up processor 44 controls the image pick-up sensor 43. Specifically, an image signal is output from the image pick-up sensor 43 by the image pick-up processor 44 reading a signal of the image pick-up sensor 43.

A correlated double sampling/automatic gain control (CDS/AGC) circuit 45 performs correlated double sampling (CDS) or automatic gain control (AGC) on an analog image signal obtained from the image pick-up sensor 43 (refer to FIG. 2). The image signal that has passed through the CDS/AGC circuit 45 is converted into a digital image signal by an analog/digital (A/D) converter 46. The digital image signal after A/D conversion is input to the processor device 15.

In the processor device 15, a first central control unit 55 configured with an image control processor operates a program in a program memory to realize functions of an image acquisition unit 50, a digital signal processor (DSP) 52, a noise reduction unit 53, an image processing switching unit 54, and an examination image acquisition unit 60.

The image acquisition unit 50 acquires a color image input from the endoscope 12. The color image includes a blue signal (B image signal), a green signal (G image signal), and a red signal (R image signal) output from the B pixel, the G pixel, and the R pixel of the image pick-up sensor 43. The acquired color image is transmitted to the DSP 52. The DSP 52 performs various types of signal processing such as a defect correction process, an offset process, a demosaic process, a matrix process, white balance adjustment, a gamma conversion process, and a YC conversion process on the received color image.

The noise reduction unit 53 performs a noise reduction process based on, for example, a moving average method or a median filter method on the color image subjected to the YC conversion process or the like by the DSP 52. The color image with reduced noise is input to the image processing switching unit 54.

The image processing switching unit 54 switches between transmission destinations of the image signal from the noise reduction unit 53 according to a set mode. Specifically, in a case where the first illumination observation mode is set, the image signal from the noise reduction unit 53 is input to a first illumination light image generation unit 70 of the examination image acquisition unit 60. In a case where the second illumination observation mode is set, the image signal from the noise reduction unit 53 is input to a second illumination light image generation unit 80. In a case where the image analysis mode is set, the image signal from the noise reduction unit 53 is input to the first illumination light image generation unit 70 and the second illumination light image generation unit 80.

In the case of the first illumination observation mode, the first illumination light image generation unit 70 performs image processing. In the case of the second illumination observation mode, the second illumination light image generation unit 80 performs image processing. In the image analysis mode, the first illumination light image generation unit 70 performs image processing on an image signal obtained by using the first illumination light, and the second illumination light image generation unit 80 performs image processing on an image signal obtained by using the second illumination light. The image processing includes 3×3 matrix processing, a gradation conversion process, a color conversion process such as three-dimensional look up table (LUT) processing, a color emphasis process, and a structure emphasis process such as spatial frequency emphasis. The image signal subjected to image processing is transmitted to the medical image processing device 11 as an examination image.

The examination image generated by the examination image acquisition unit 60 of the processor device 15 is transmitted to the medical image processing device 11. The medical image processing device 11 includes an image input unit 100, a classifier 110, a display image generation unit 150, a notification control unit 210, a display control unit 200, and a second central control unit 101 (refer to FIG. 2).

In the medical image processing device 11, the second central control unit 101 configured with an image analysis processor operates a program in a program memory to realize functions of the image input unit 100, the classifier 110, the display image generation unit 150, the notification control unit 210, and the display control unit 200.

Figure 7:
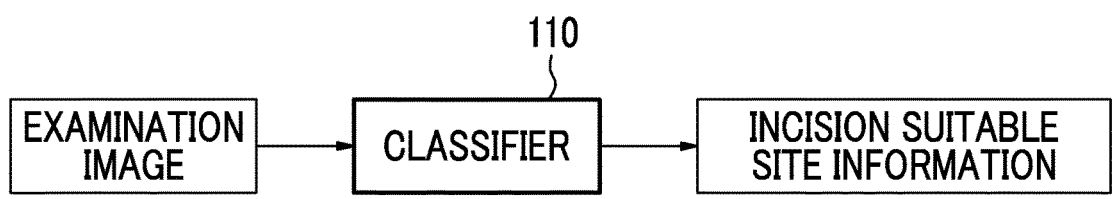
FIG. 7 is a block diagram showing a function of a classifier that outputs incision suitable site information.
Figure 8:
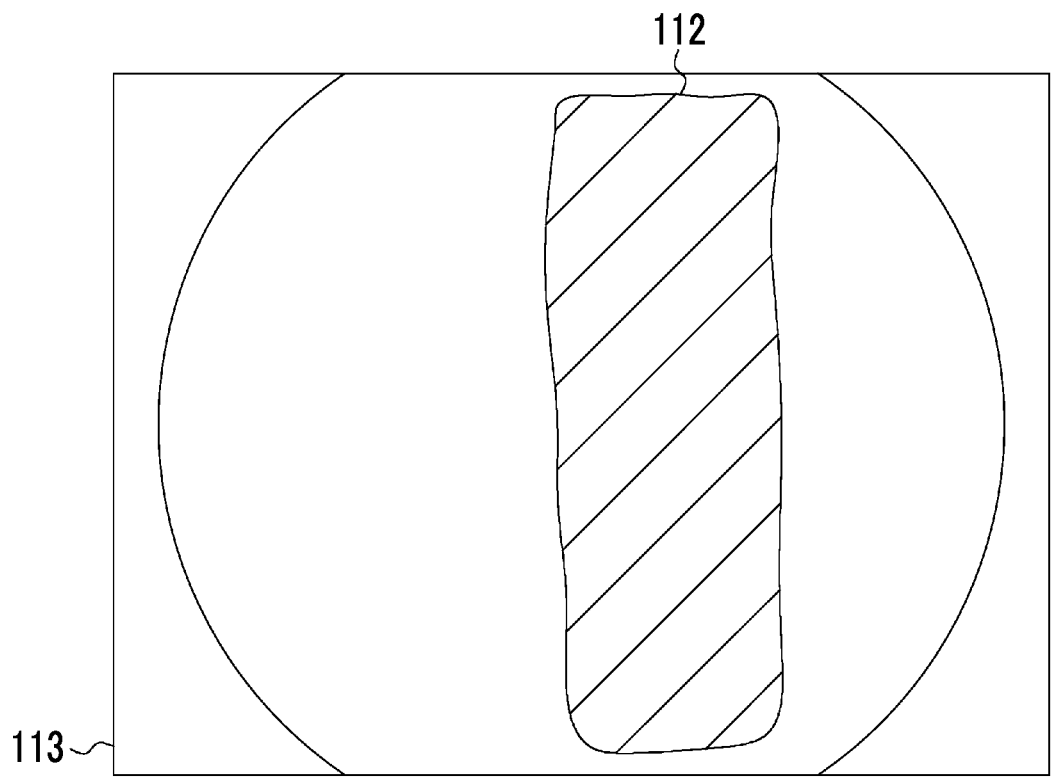
FIG. 8 is an image diagram showing an example of a display image.

The examination image is transmitted to the image input unit 100 of the medical image processing device 11 (refer to FIG. 2). The image input unit 100 inputs the examination image to the classifier 110. The classifier 110 identifies an incision suitable site that is a site suitable for incision in ESD in a subject included in the input examination image. Identification is to distinguish between an incision suitable site and an incision unsuitable site, and to select the incision suitable site from the examination image. As shown in FIG. 7, the classifier 110 identifies the incision suitable site on the basis of the examination image and outputs incision suitable site information regarding the incision suitable site. The incision suitable site information is used to generate a display image 113 that displays the incision suitable site 112 on the display 17, as shown in FIG. 8.

The classifier 110 performs learning by using a learning image. The classifier 110 is a learning model that performs learning by using a learning image through machine learning. The learning image is an image in which various types of information are associated with a medical image. Association is to add information to a learning image.

The incision suitable site is a site suitable for incision of the submucosal layer in ESD. ESD goes through the steps of (1) marking around a tumor, (2) local injection into the submucosal layer, (3) incision of the mucous membrane, (4) peeling of the submucosal layer, and (5) hemostasis, and a malignant tumor or the like is resected under the endoscope. Identification of the incision suitable site is important in (4) peeling of the submucosal layer. A local injection solution is locally injected into the deeper submucosal layer of the marked lesion part to make the lesion part float from the surrounding mucous membrane, and the mucosal epithelium outside the marking is incised with a treatment tool such as an electric scalpel. Thus, the deep submucosal layer is visible, and the lesion part can be peeled off. Here, in a case where incision or peeling is made deep in the mucous membrane, the incision or the peeling reaches the muscular layer deeper in the submucosal layer, and in a case where the incision is made deeper than this, the muscular layer and the thin serosa outside the muscular layer are broken, and thus a hole is formed in the digestive tract, that is, penetration occurs. Therefore, by distinguishing the muscular layer in advance, it is possible to prevent the muscular layer from being incised erroneously and to support ESD. By learning a position of the muscular layer, which is a site unsuitable for incision, the classifier 110 can identify the incision suitable site and output the identified result as incision suitable site information.

The incision suitable site information is information output by the classifier 110 to which the examination image is input. The learning image used for learning of the classifier 110 is associated with information regarding a position of the muscular layer in the subject. The position of the muscular layer includes three-dimensional information indicating a thickness of the submucosal layer covering the surface of the muscular layer (a thickness from the submucosal layer to the muscular layer) in addition to two-dimensional information indicating a range of the muscular layer region in the learning image. The thicker the submucosal layer on the surface of the muscular layer, the lower the risk of incising the muscular layer, and thus the thick submucosal result is a site suitable for incision. Such a thick submucosal layer may be an incision suitable site. Conversely, the thinner the submucosal layer, the higher the risk of perforation, and thus the thin submucosal layer is not suitable for incision. The muscular layer of which the submucosal layer on the surface is thin and which is substantially exposed is at high risk and not suitable for incision.

Figure 9:
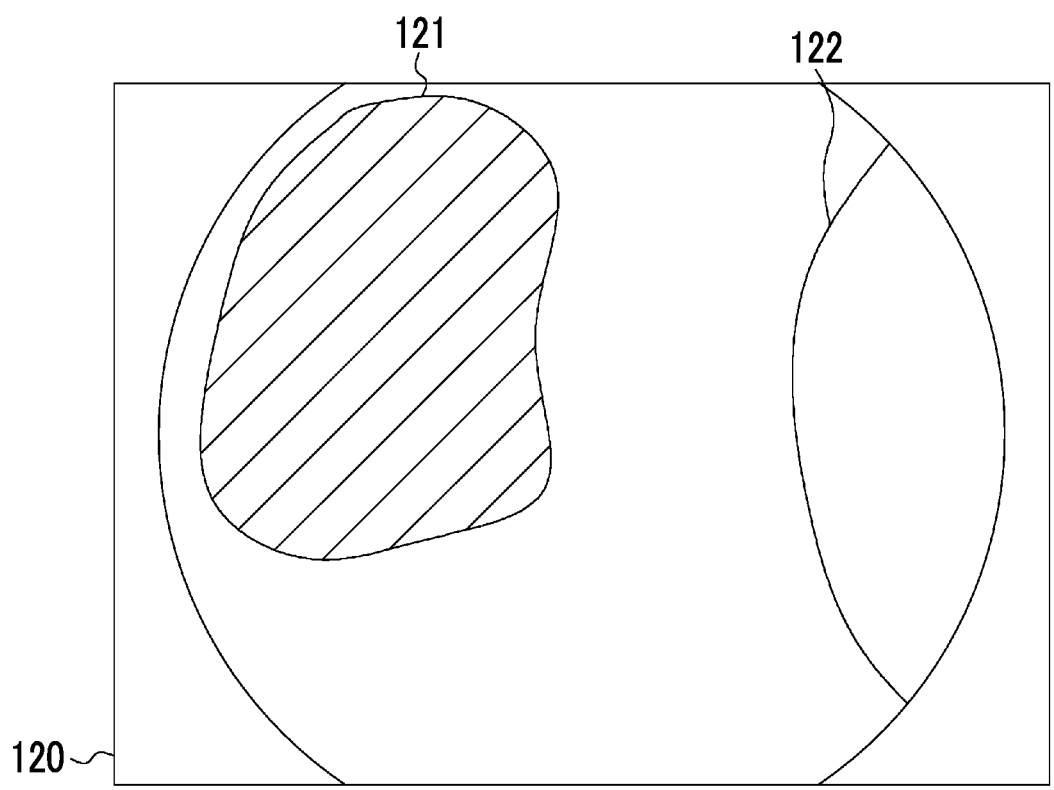
FIG. 9 is an image diagram showing an example of a learning image including a region of a substantially exposed muscular layer.
Figure 10:
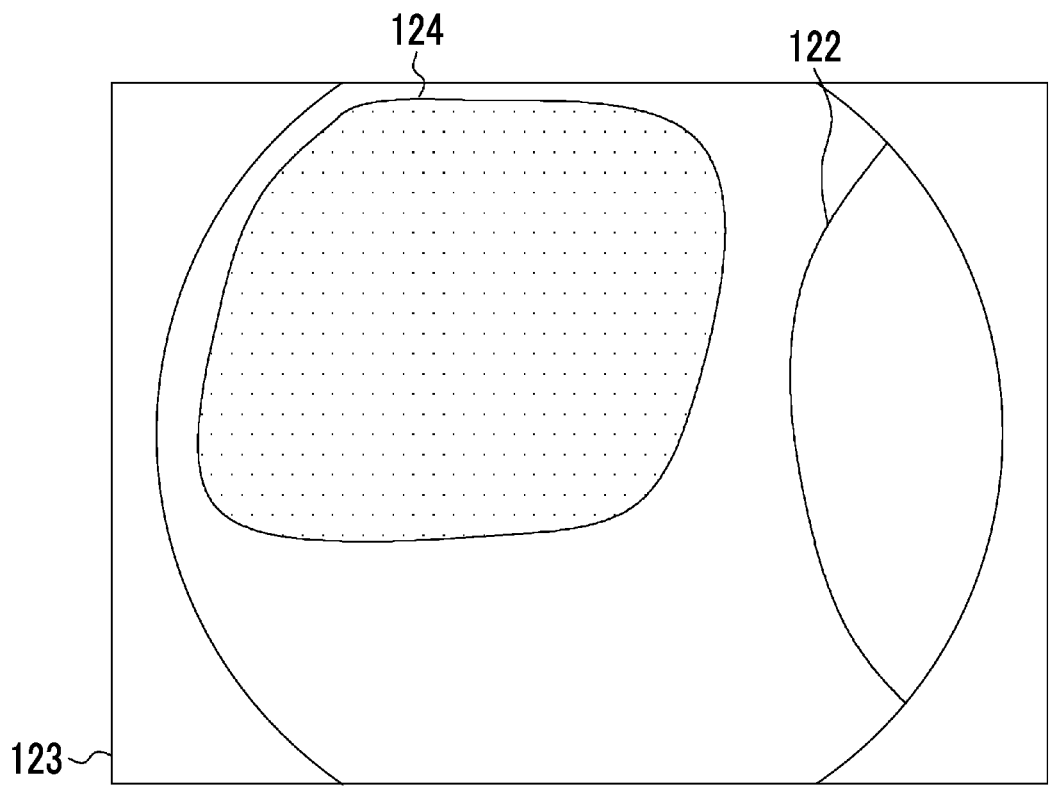
FIG. 10 is an image diagram showing an example of a learning image including a region in which a submucosal layer covers a muscular layer.

As shown in FIG. 9, in a case of a learning image 120 including a region 121 of the substantially exposed muscular layer, the region of the muscular layer is associated as a two-dimensional position of the muscular layer. As shown in FIG. 10, in a case of a learning image 123 including a region 124 in which the submucosal layer covers the muscular layer, the degree of thickness from the submucosal layer to the muscular layer is associated as a three-dimensional position of the muscular layer in the learning image. The degree of thickness from the submucosal layer to the muscular layer may be a semi-quantitative degree such as "thin", "medium" and "thick", or a quantitative degree such as "10 μm" and "100 μm". The position of the muscular layer in the subject includes the absence of the position of the muscular layer, that is, the subject does not include the muscular layer. A lesion part 122 is preferably included in the learning image. As will be described later in detail, in ESD, both a distance from a position where peeling is performed to the muscular layer and a distance to the lesion part are important in peeling of the submucosal layer.

The association of the position of the muscular layer with the learning image may be performed by a skilled doctor, or may be automatically performed by a device other than the medical image processing device 11. The information output by the classifier 110 or another classifier may be associated with the examination image, and the examination image may be used for learning of the classifier 110 as a learning image.

Although a relatively large lesion can be resected under the endoscope in ESD, a procedure is difficult and there is a risk that the muscular layer may be incised and perforated without the operator's awareness. In particular, it is difficult for an operator with a small number of ESD cases to determine a position of the muscular layer on the examination image. Therefore, the classifier 110 that has performed learning by using the learning image associated with the position of the muscular layer automatically identifies an incision suitable site suitable for incision on the basis of the examination image, and outputs incision suitable site information, the image processing device 11 controls the output, and thus it is possible to identify a site that can be safely incised. With the above configuration, it is possible to prevent the muscular layer from being incised erroneously and to support ESD.

Figure 11:
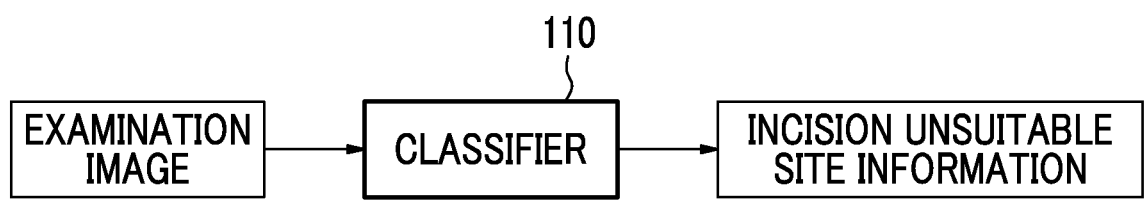
FIG. 11 is a block diagram showing a function of a classifier that outputs incision unsuitable site information.

As shown in FIG. 11, the classifier 110 preferably identifies an incision unsuitable site that is a site unsuitable for incision in ESD in the subject included in the input examination image, and outputs incision unsuitable site information regarding the incision unsuitable site. Incision unsuitable sites include fibrosis that is indistinguishable from the muscular layer, the muscular layer of which the surface is not covered by the submucosal layer, and the submucosal layer of which a distance to a lesion part that is far from the muscular layer is short and in which the lesion part may not be resected.

Figure 12:
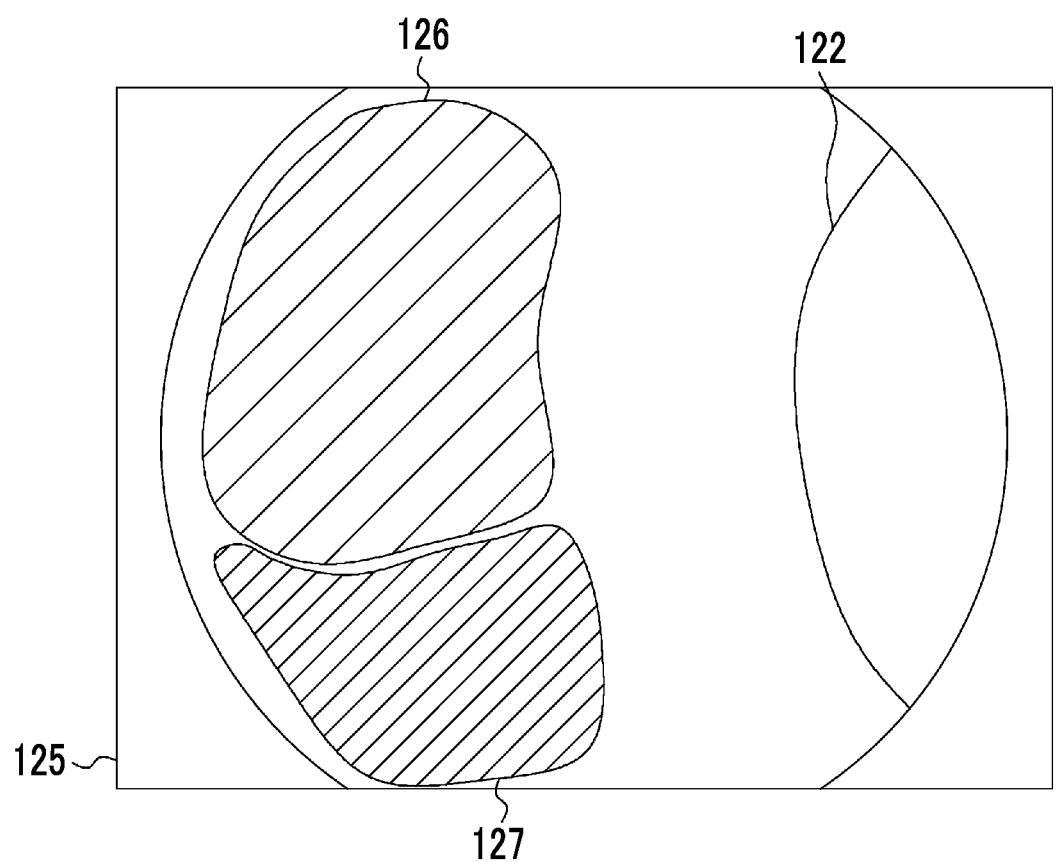
FIG. 12 is an image diagram showing an example of a learning image including fibrosis.

It is preferable that the learning image used for learning of the classifier 110 that outputs the incision unsuitable site information is associated with a position of fibrosis. For example, as shown in FIG. 12, a learning image 125 including fibrosis is associated with a position of a muscular layer 126 and a position of fibrosis 127. The learning image 125 preferably includes the lesion part 122. The fibrosis is the site where an extracellular matrix including collagen fibers increases. The fibrosis itself can be incised without problems, but developed fibrosis may be indistinguishable from the muscular layer. In a case where such fibrosis, which is indistinguishable from the muscular layer, is present on the examination image together with the muscular layer, it is preferable to identify the muscular layer as an incision unsuitable site because there is a risk of erroneously incising the muscular layer. Fibrosis that can be completely distinguished from the muscular layer and has a low risk of being mistaken for the muscular layer may be associated with a learning image and learned by the classifier 110, and the classifier 110 may identify such fibrosis as an incision suitable site.

Figure 13:
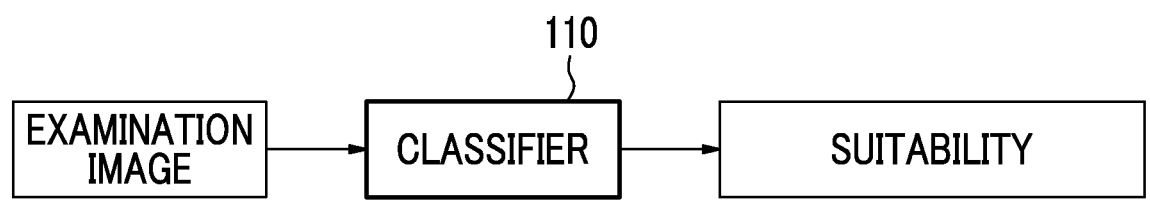
FIG. 13 is a block diagram showing a function of the classifier that outputs suitability.

As shown in FIG. 13, the classifier 110 preferably identifies an incision suitable site and an incision unsuitable site by the suitability, and outputs incision suitable site information as the suitability. The suitability becomes higher for a site identified to be able to be more safely incised, such as a thick submucosal layer on the surface of the muscular layer, and becomes lower for a site identified not to be able to be safely incised, such as an exposed muscular layer at risk of perforation. Specifically, the suitability varies depending on a position of the muscular layer, a position of fibrosis, the similarity to the muscular layer of fibrosis, a distance from the submucosal layer to the muscular layer, a distance from the submucosal layer to the lesion part, and the like. By identifying the suitability related to evaluation of an incision suitable site and an incision unsuitable site, the degree of safety of incision can be identified.

Figure 14:
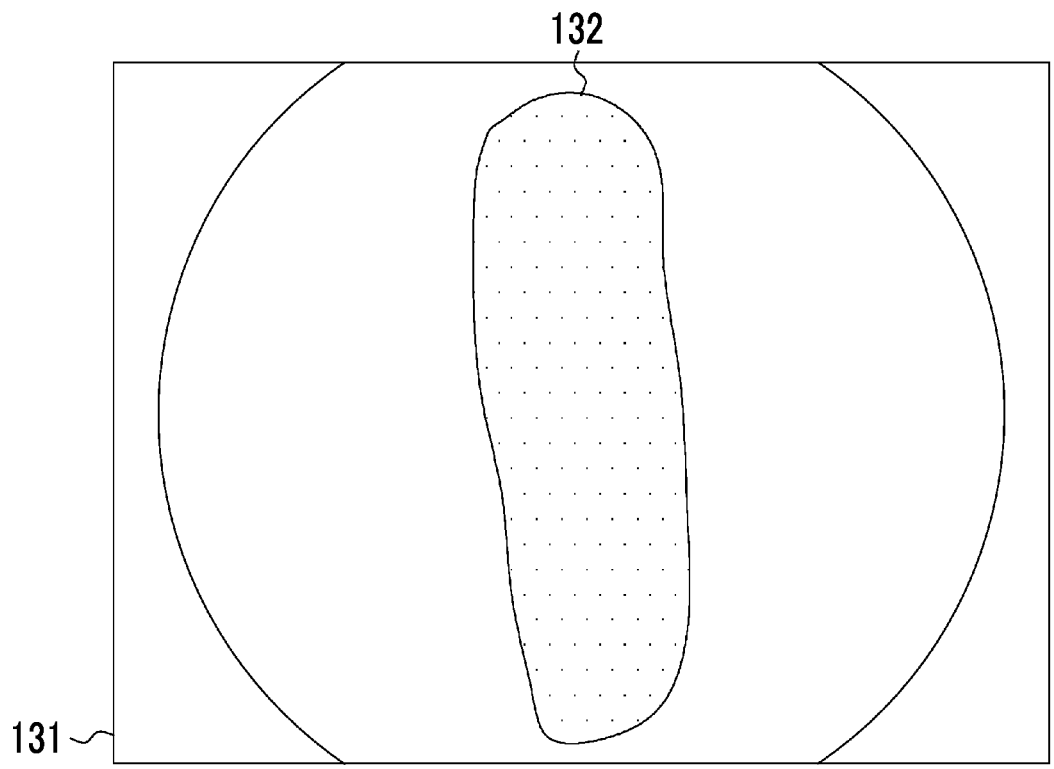
FIG. 14 is an image diagram showing an example of a learning image in which a local injection solution is not locally injected into the submucosal layer.
Figure 15:
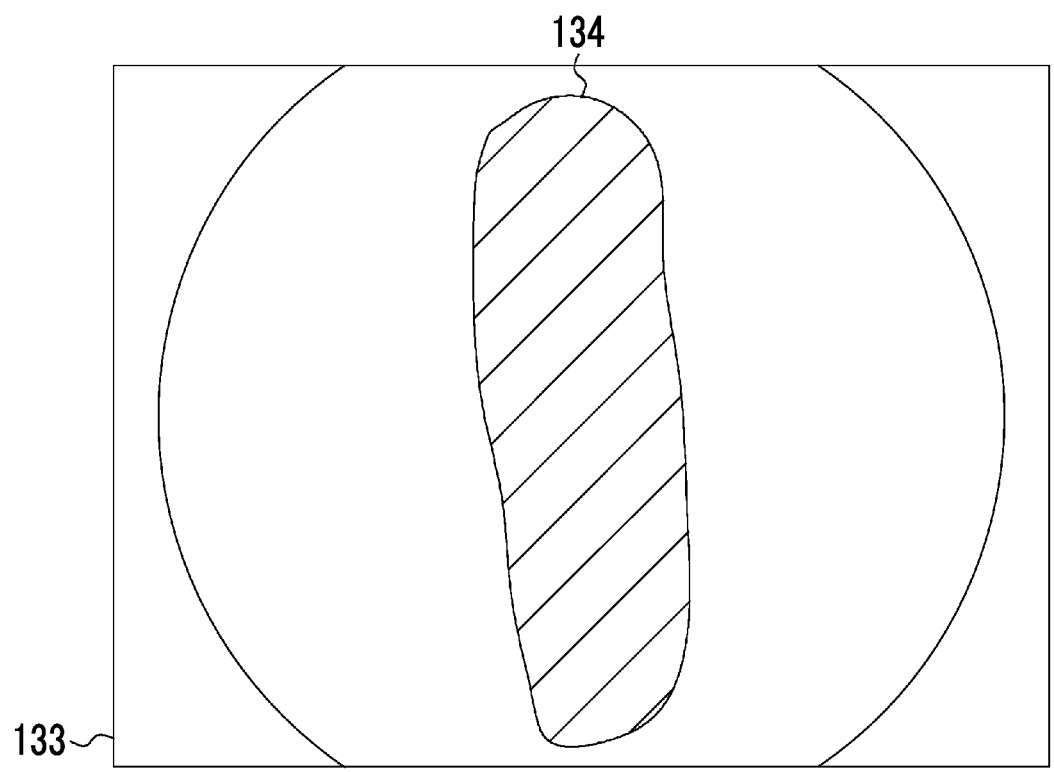
FIG. 15 is an image diagram showing an example of a learning image in which a local injection solution is locally injected into the submucosal layer.

It is preferable that the learning image is associated with a position of the submucosal layer into which a local injection solution is locally injected in the subject. FIG. 14 shows a learning image 131 in which a local injection solution is not locally injected into the submucosal layer, and FIG. 15 shows a learning image 133 in which the local injection solution containing no staining solution is locally injected into the submucosal layer. In FIG. 14, the submucosal layer 132 into which the local injection solution is not locally injected is visible as a white mesh. On the other hand, in the learning image 133 in which the local injection solution containing no staining solution is locally injected in FIG. 15, the submucosal layer 134 into which the local injection solution not containing the staining solution is locally injected is clearly visible and thus a site suitable for incision can be identified more easily. Hereinafter, among submucosal layers, a submucosal layer particularly suitable for incision will be referred to as a peeling layer. The peeling layer is an incision suitable site with a particularly high suitability. In the image in which the local injection solution is locally injected as shown in FIG. 15, the presence of the peeling layer or a thickness up to the muscular layer can be more easily identified, and thus the analysis accuracy of the classifier 110 is improved. A learning image may be the learning image 131 in which the local injection solution is not locally injected into the submucosal layer in the subject as shown in FIG. 14.

Figure 16:
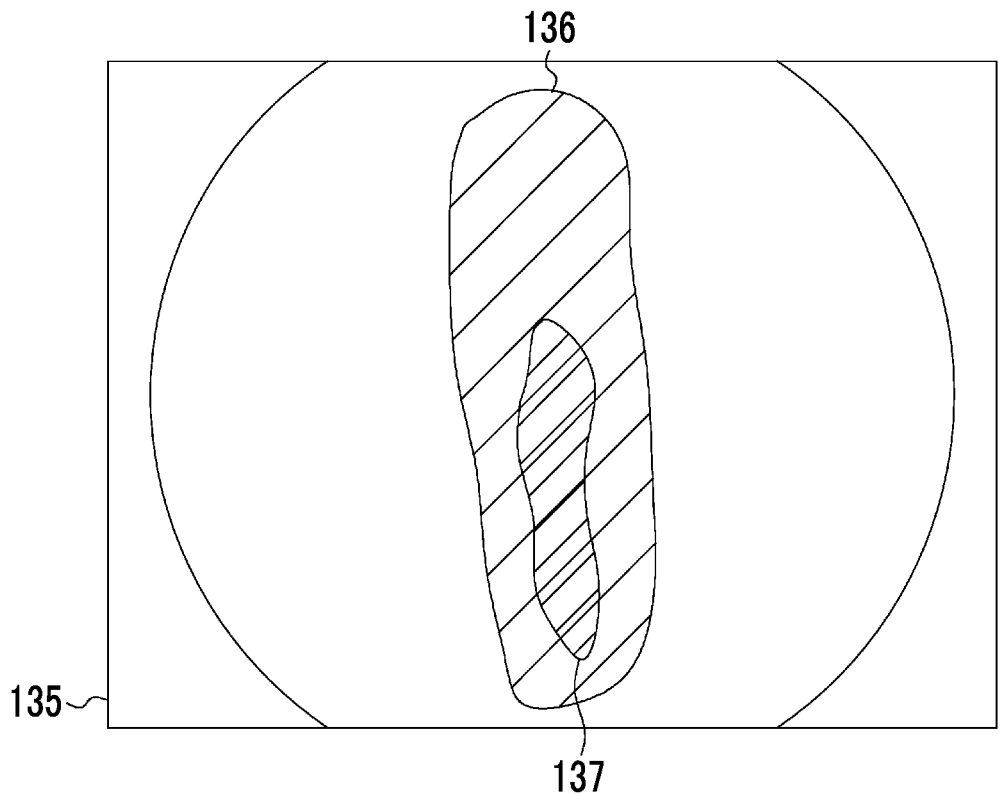
FIG. 16 is an image diagram showing an example of a learning image in which a local injection solution containing a low concentration of indigo carmine is locally injected into the submucosal layer.

It is preferable that the learning image is associated with a position of the submucosal layer into which the local injection solution containing the staining solution is locally injected in the subject. The staining solution is preferably indigo carmine. In a case where the local injection solution contains indigo carmine, it is preferable that a concentration of indigo carmine is associated with the learning image. FIG. 16 shows a learning image 135 in which a local injection solution containing a low concentration of indigo carmine was locally injected into the submucosal layer. In the learning image 135 shown in FIG. 16, the submucosal layer 136 into which the indigo carmine is locally injected is visible as bluish and transparent, and the peeling layer 137 in which the local injection solution is accumulated and which can be incised particularly safely is visible in darker blue than the surroundings. It is preferable that the learning image 135 is associated with the submucosal layer 136 in which a local injection solution containing indigo carmine is locally injected and the peeling layer 137 that can be particularly safely incised.

Figure 17:
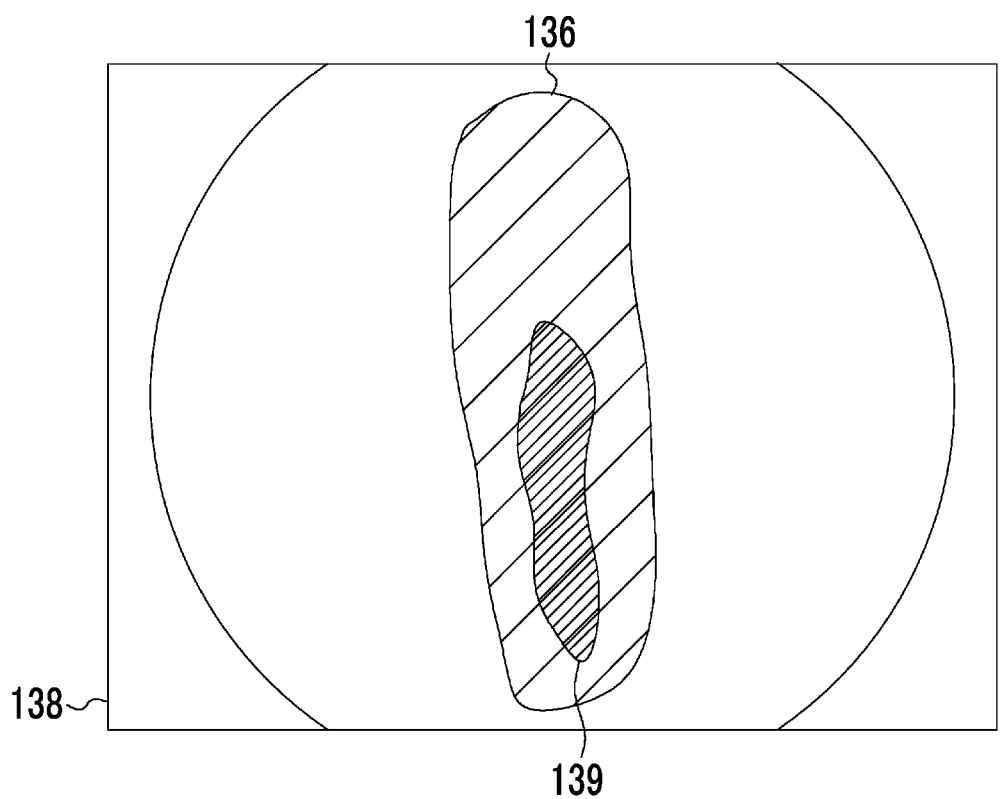
FIG. 17 is an image diagram showing an example of a learning image in which a local injection solution containing a high concentration of indigo carmine is locally injected into the submucosal layer.

FIG. 17 shows a learning image 138 in which a local injection solution containing a high concentration of indigo carmine is locally injected. In the learning image 138 shown in FIG. 17, in the same manner as in FIG. 16, the submucosal layer 136 into which the local injection solution containing indigo carmine is locally injected is visible as bluish and transparent, but the peeling layer 139 that can be incised particularly safely is visible in deeper blue than in the case of low concentration. The local injection solution containing a high concentration of indigo carmine is, for example, a local injection solution obtained by adding 0.5 ml of indigo carmine to 20 ml of a stock solution of Mucoup®. This high concentration of indigo carmine local injection solution is a local injection solution in which an indigo carmine concentration is adjusted such that the peeling layer is more easily visible than in a normal local injection solution. It is preferable that the learning image 138 is associated with the submucosal layer 136 into which a local injection solution containing indigo carmine is locally injected and the peeling layer 139 which can be particularly safely incised. As shown in FIGS. 16 and 17, from the learning image in which the local injection solution containing indigo carmine is locally injected into the submucosal layer, the peeling layer that can be safely incised is easily visible, and thus the analysis accuracy of the classifier 110 is improved.

Figure 18:
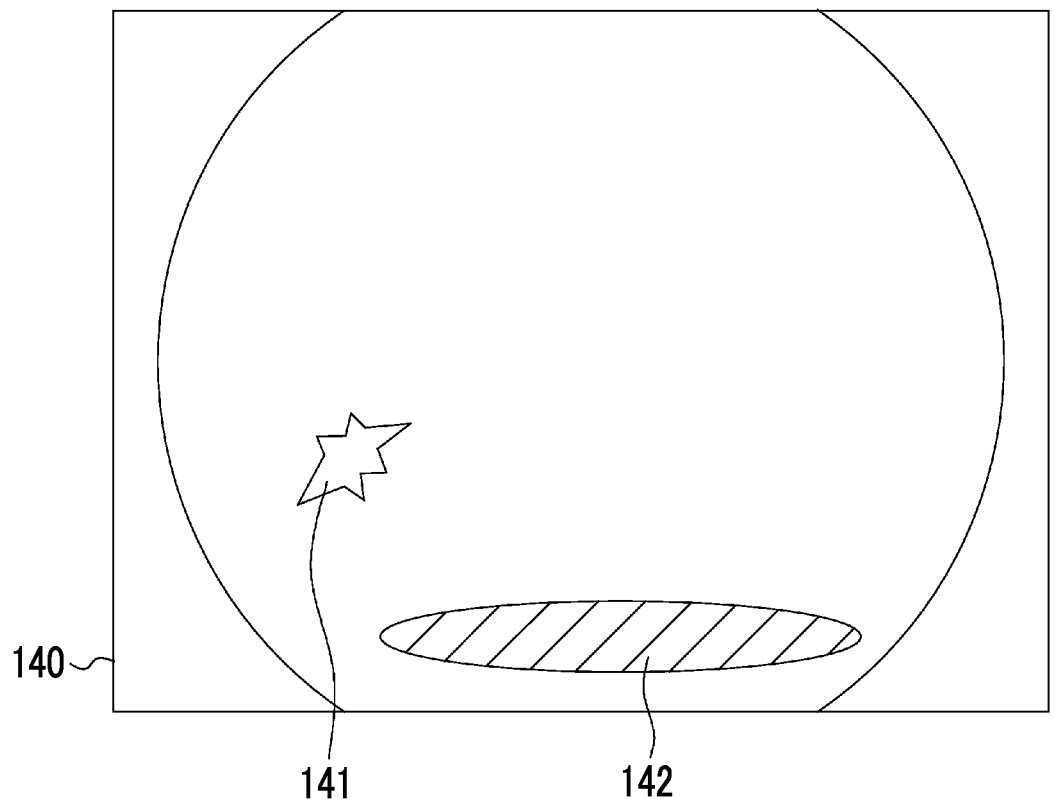
FIG. 18 is an image diagram showing an example of a learning image including a cautery scar and coagulated blood.

The learning image is preferably a learning image associated with the presence or absence of a cautery scar and/or coagulated blood in a subject. FIG. 18 shows a learning image 140 that includes a cautery scar 141 and coagulated blood 142. The cautery scar 141 and the coagulated blood 142 reduce the visibility of the entire examination image including the muscular layer, fibrosis, the submucosal layer including a peeling layer, and the like. Thus, by causing in advance the classifier 110 to perform learning by using the learning image 140 including the cautery scar 141 and the coagulated blood 142, the classifier 110 can identify a safe incision site even in a situation in which ESD is difficult to perform due to the presence of the cautery scar 141 and the coagulated blood 142.

Figure 19:
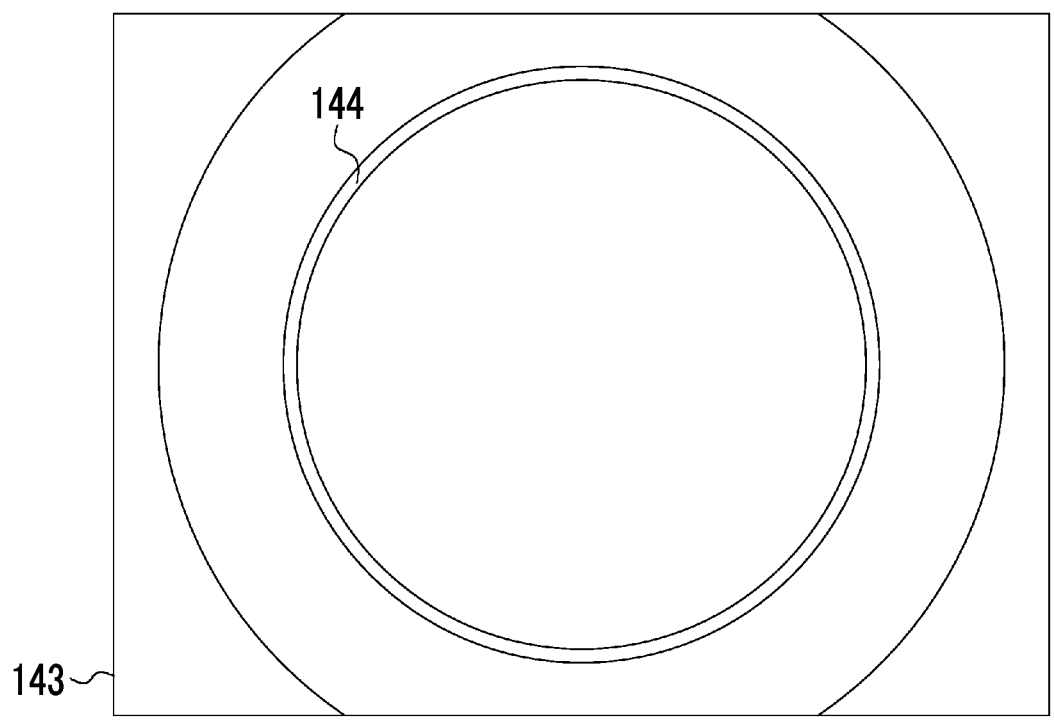
FIG. 19 is an image diagram showing an example of a learning image in which an edge of a hood is included in a field of view.

The learning image is preferably a learning image associated with a position of the hood attached to the tip of the endoscope with respect to the subject is associated. FIG. 19 shows a learning image 143 in which an edge 144 of the hood is included in a field of view. Since a hood is often used in a case where ESD is performed, it is preferable to use only the learning image 143 in which the edge 144 of the hood is included in the field of view as a learning image in a case where the classifier 110 performs learning. In a case where the hood is attached, it is determined that a distance between the tip part 12d of the endoscope 12 and the subject is 3 to 5 mm Since the subject to which ESD is applied can be clearly visible at this distance, an examination image including the hood in the field of view (a distance between the tip 12d of the endoscope 12 and the subject is 3 to 5 mm) is preferably used as a learning image.

In a case where the hood is attached to the tip part 12d of the endoscope 12 and the edge part 144 of the hood is captured in an image, the visibility of the edge part 144 of the hood and its outer portion is reduced. A position of the hood included in the learning image 143 as shown in FIG. 19 is associated with the learning image 143 and used for learning of the classifier 110, the portions with reduced visibility that are the edge part 144 of the hood and its outside are excluded from analysis targets, and thus the analysis accuracy of the classifier 110 can be improved.

It is preferable that the learning image is associated with a distance from the submucosal layer to the muscular layer and a distance from the submucosal layer to a lesion part. The muscular layer of which the submucosal layer on the surface is thin increases the risk of perforation. Even though the submucosal layer is far from the muscular layer, in a case where the submucosal layer is close to a lesion part (within 500 μm), there is a risk that the lesion part cannot be completely resected. Therefore, it is preferable to identify a site where a distance from the submucosal layer to the muscular layer is short and a site where a distance from the submucosal layer to the lesion part is short as an incision unsuitable site, and output the incision unsuitable site as incision unsuitable site information. On the other hand, it is preferable to identify the submucosal layer at an appropriate distance from the muscular layer and the lesion part as an incision suitable site and output the incision suitable site as incision suitable site information. It is preferable to output a distance from the submucosal layer to the muscular layer as incision suitable site information. The distance may be a semi-quantitative degree such as "near", "medium" and "far", or a quantitative degree such as "10 μm" and "100 μm".

It is preferable to use deep learning for machine learning to generate a learning model, and, for example, it is preferable to use a multi-layer convolutional neural network. In addition to deep learning, machine learning includes a decision tree, a support vector machine, a random forest, regression analysis, supervised learning, semi-unsupervised learning, unsupervised learning, reinforcement learning, deep reinforcement learning, learning using neural networks, a hostile generation network, and the like.

Figure 20:
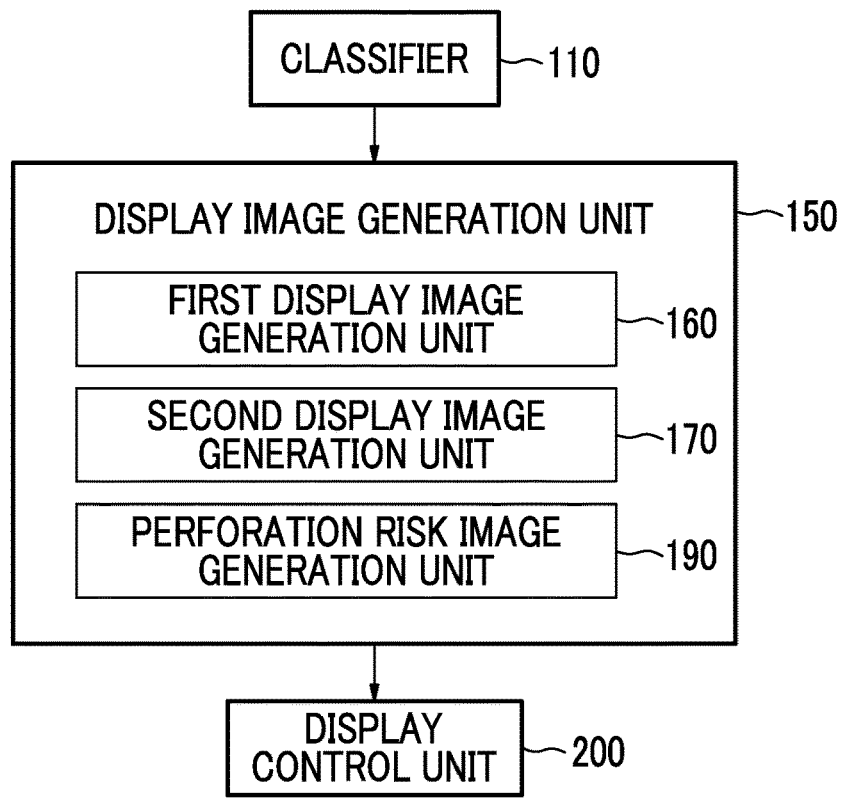
FIG. 20 is a block diagram showing a function of a display image generation unit.

FIG. 20 shows signals transmitted and received by the display image generation unit 150. The incision suitable site information, the incision unsuitable site information, and the suitability output by the classifier 110 are transmitted to the display image generation unit 150 (refer to FIG. 2). The display image generation unit 150 includes a first display image generation unit 160, a second display image generation unit 170, and a perforation risk image generation unit 190. The display image generation unit 150 transmits an image signal to the display control unit 200.

Figure 21:
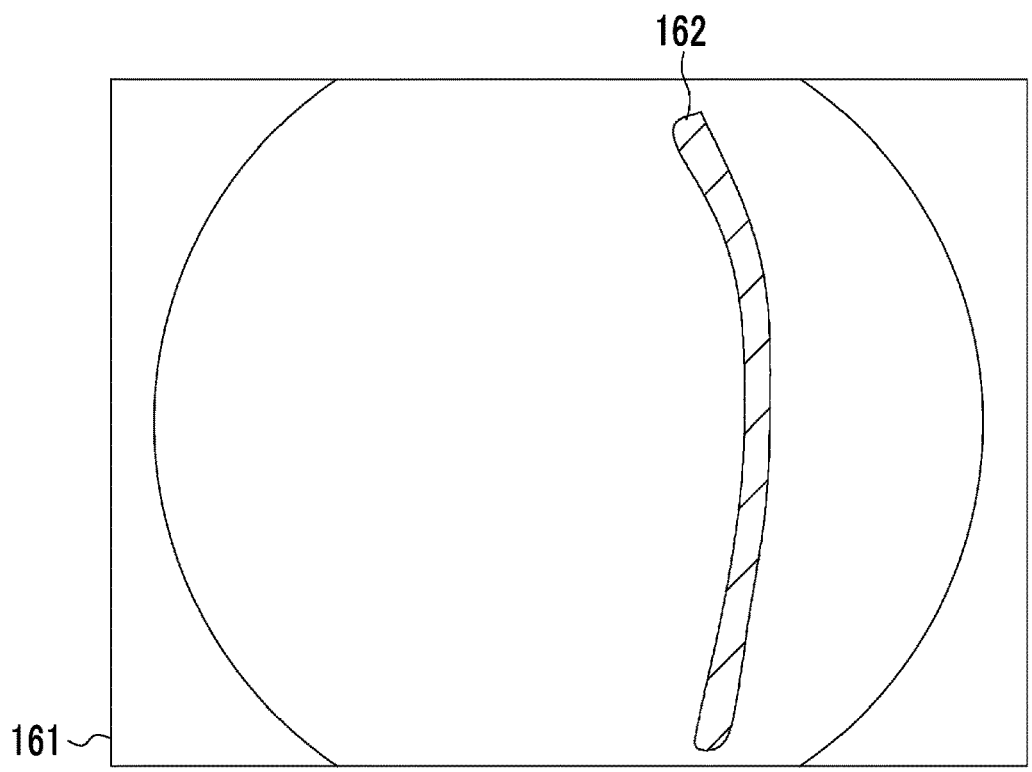
FIG. 21 is an image diagram showing an example of a first display image.

The first display image generation unit 160 generates a first display image 161 indicating the incision suitable site as an image on the basis of the incision suitable site information. FIG. 21 shows a first display image. In a first display image 161, it is preferable that a site suitable for incision is indicated with a color, a symbol, or a figure. In particular, it is preferable to indicate the site suitable for the incision with a line. In FIG. 21, a peeling layer 162 is indicated with a line. The first display image 161 is transmitted to the display control unit 200, superimposed on and examination image, and displayed on the display 17. With the above configuration, it is possible to positively present a site that can be safely incised to an operator during ESD.

Figure 22:
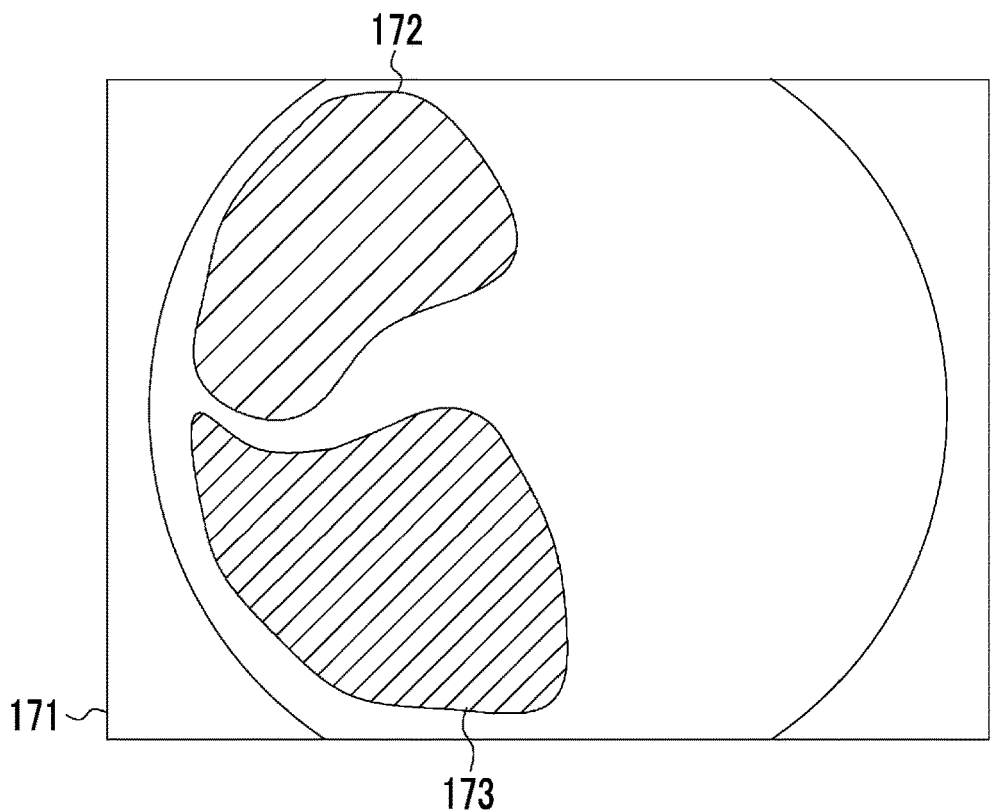
FIG. 22 is an image diagram showing an example of a second display image.

The second display image generation unit 170 generates a second display image 171 indicating the incision unsuitable site as an image on the basis of the incision unsuitable site information. FIG. 22 shows the second display image 171. In FIG. 22, a muscular layer 172 and fibrosis 173 identified as incision unsuitable sites are displayed. The second display image 171 is transmitted to the display control unit 200, superimposed on an examination image, and displayed on the display 17. With the above configuration, it is possible to positively present a site that is dangerous for incision to an operator during ESD.

Figure 23:
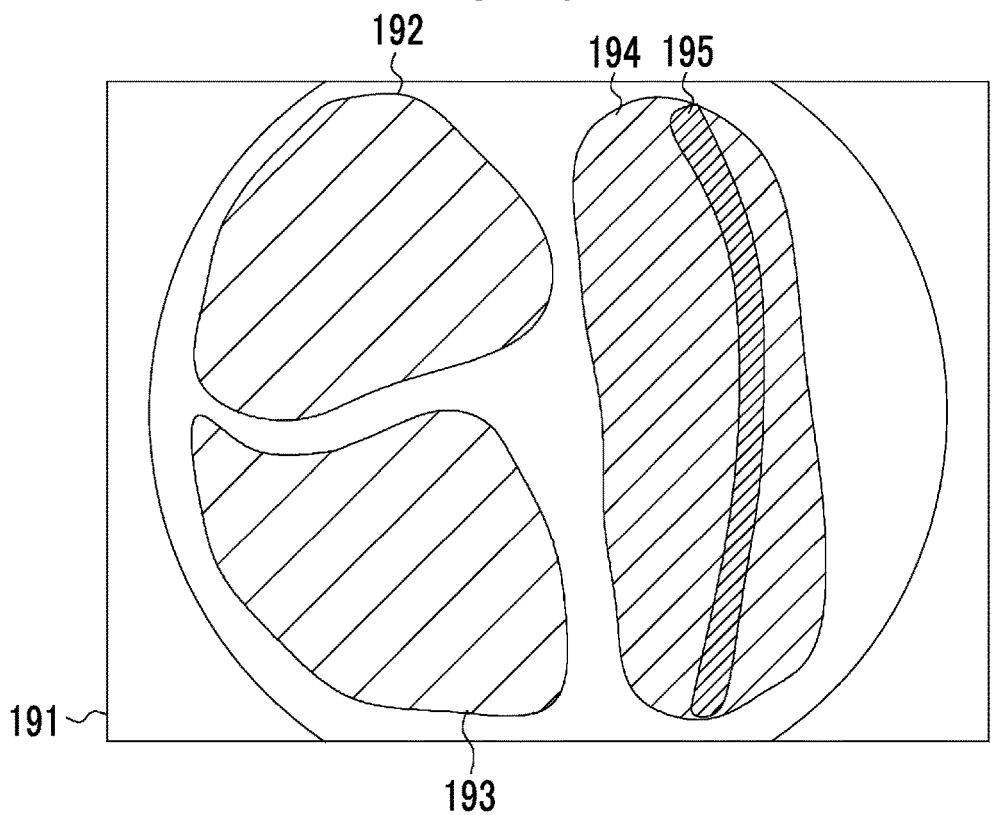
FIG. 23 is an image diagram showing an example of a perforation risk image.

The perforation risk image generation unit 190 generates a perforation risk image 191 indicating the suitability as an image on the basis of the incision suitable site information, the incision unsuitable site information, and the suitability. FIG. 23 shows a perforation risk image 191. In FIG. 23, the perforation risk image 191 is displayed as a heat map in which classifications are color-coded (indicated by the density of diagonal lines) according to the suitability. For example, the muscular layer 192 and fibrosis 193, which are not suitable for incision and have low suitability, are displayed in red, the submucosal layer 194 other than the peeling layer having intermediate suitability is displayed in green, and the peeling layer 195 with high suitability is displayed in blue. Color coding is not limited to this. A probability of perforation may be displayed by using the color coding as a legend. The probability of perforation may be displayed only numerically. The perforation risk image 191 is transmitted to the display control unit 200, superimposed on an examination image, and displayed on the display 17. With the above configuration, in addition to a site that can be safely incised a dangerous site for incision can be presented to an operator during ESD.

Figure 24:
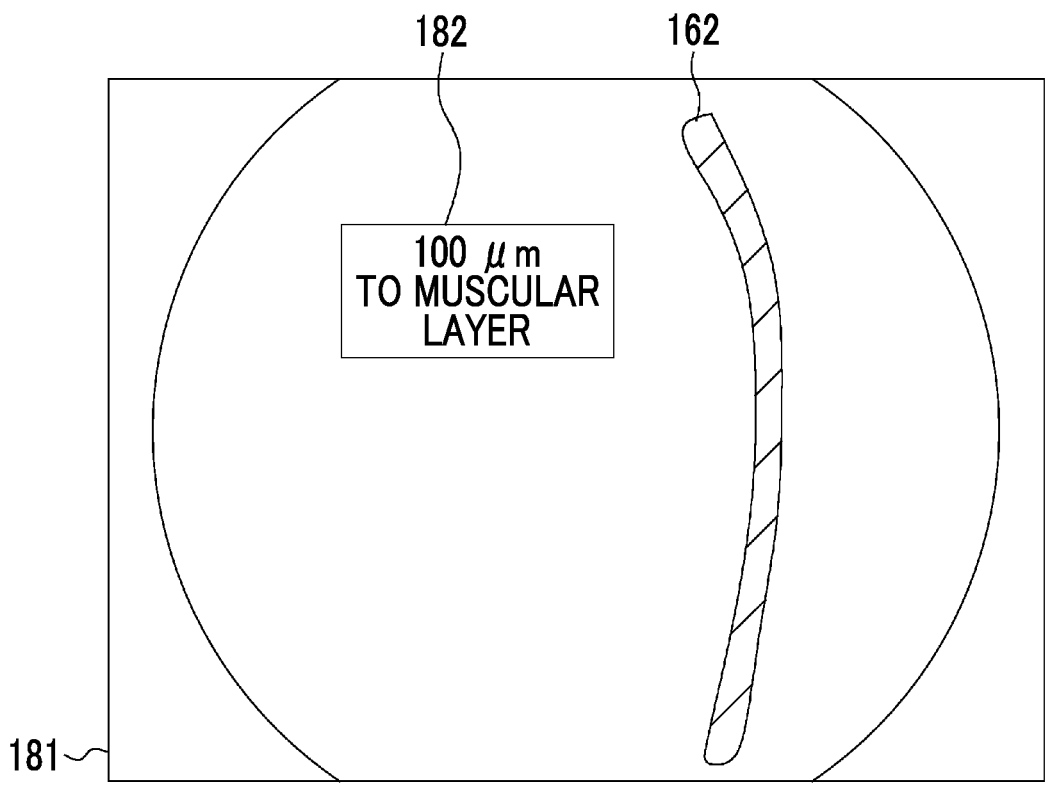
FIG. 24 is an image diagram showing an example of an inter-tissue distance display image.

In a case where a distance from the submucosal layer to the muscular layer is included in the incision suitable site information, it is preferable that the display control unit 200 superimposes a distance 182 from the peeling layer to the muscular layer on the examination image and display an inter-tissue distance image 181 as shown in FIG. 24. With the above configuration, it is possible to present a safe incision distance to an operator during ESD.

The first display image 161 and the second display image 171, the inter-tissue distance display image 181, and the perforation risk image 191 may be combined and superimposed on the examination image.

Figure 25:
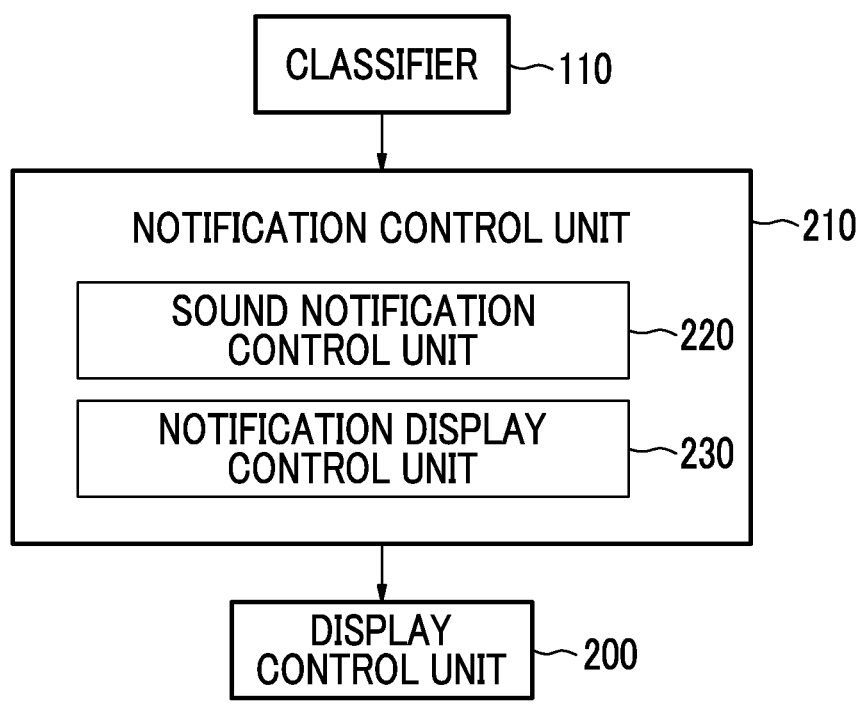
FIG. 25 is a block diagram showing a function of a notification control unit.

FIG. 25 shows signals transmitted and received by the notification control unit 210. The incision suitable site information, the incision unsuitable site information, and the suitability output by the classifier 110 are transmitted to the notification control unit 210 (refer to FIG. 2). The notification control unit 210 includes a sound notification control unit 220 and a notification display control unit 230. In a case where the incision unsuitable site information in which the incision unsuitable site is included in an examination image is received, the sound notification control unit 220 transmits a sound notification signal and emits a warning sound from a speaker (not shown) to provide a notification. A threshold value for notification may be set for the suitability, and a warning sound may be emitted in a case where there is an incision unsuitable site of which the suitability is less than the threshold value. A threshold value may be freely set. With the above configuration, an operator can more easily and visually recognize the presence of a site unsuitable for incision.

Figure 26:
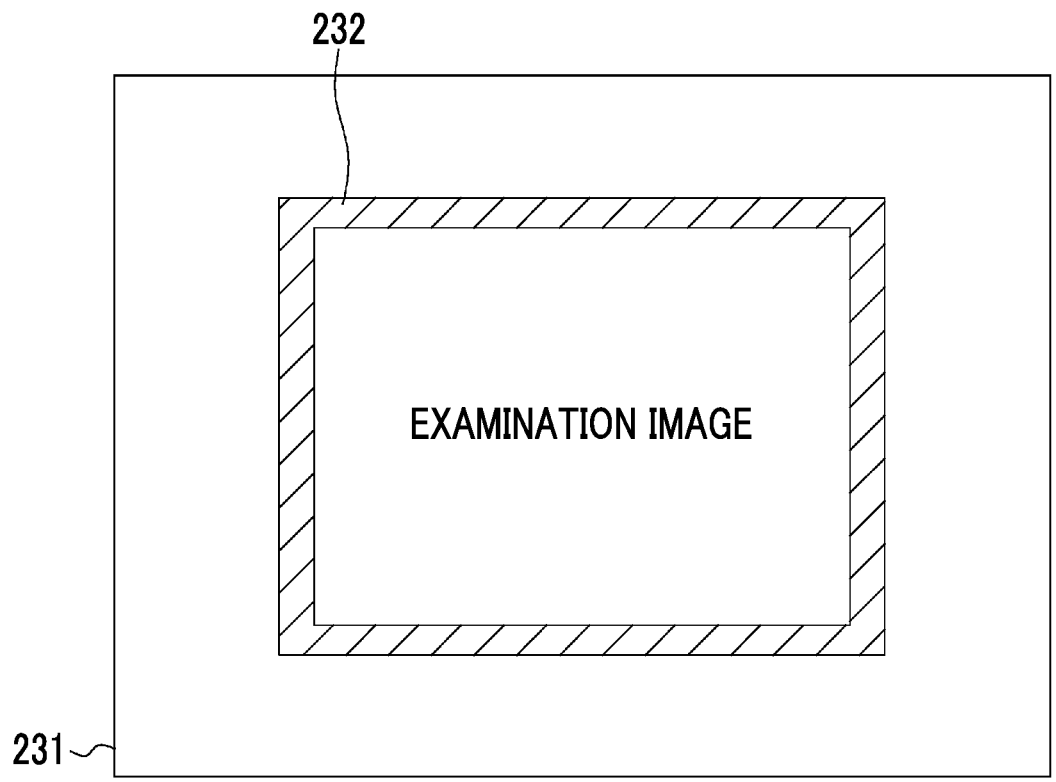
FIG. 26 is an image diagram showing an example of a warning display screen in which a frame is provided around an examination image.
Figure 27:
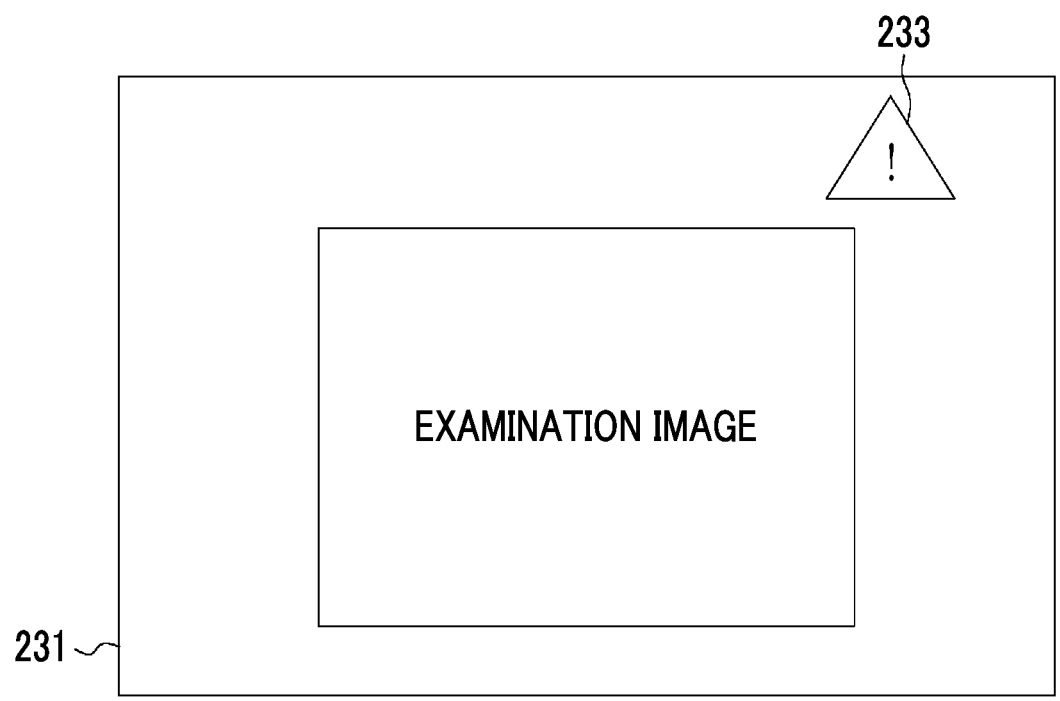
FIG. 27 is an image diagram showing an example of a warning display screen using a warning mark.

FIGS. 26 and 27 show a warning display screen 231 generated by the notification display control unit 230. In a case where the incision unsuitable site information in which the incision unsuitable site is included in an examination image is received, the notification display control unit 230 transmits a notification display signal to the display control unit 200. For example, as shown in FIG. 26, the notification display control unit 230 provides a frame 232 around the examination image to notify that a treatment tool such as an electric scalpel is present near the incision unsuitable site. A form of the frame is not limited to surrounding the entire periphery of the examination image. As shown in FIG. 27, a warning mark 233 may be used for display. A form of the warning mark 233 is not limited to this. A threshold value for notification may be set for the suitability, and a notification may be displayed in a case where there is an incision unsuitable site of which the suitability is less than the threshold value. A threshold value may be freely set.

Figure 28:
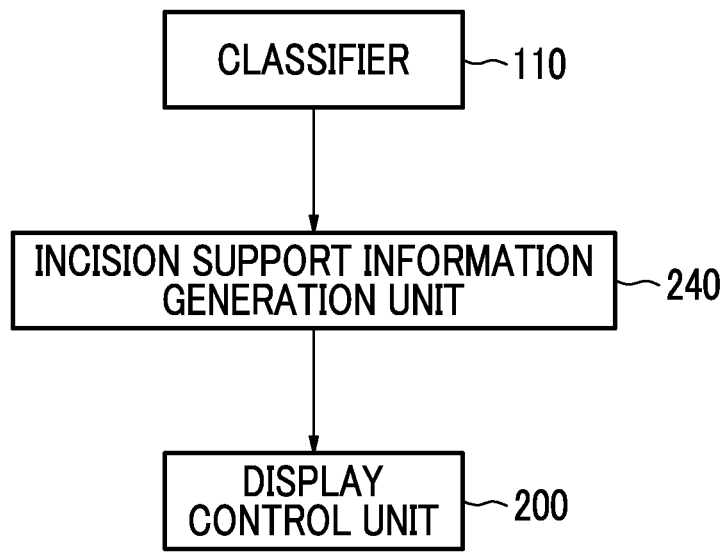
FIG. 28 is a block diagram showing a function of an incision support information generation unit.
Figure 29:
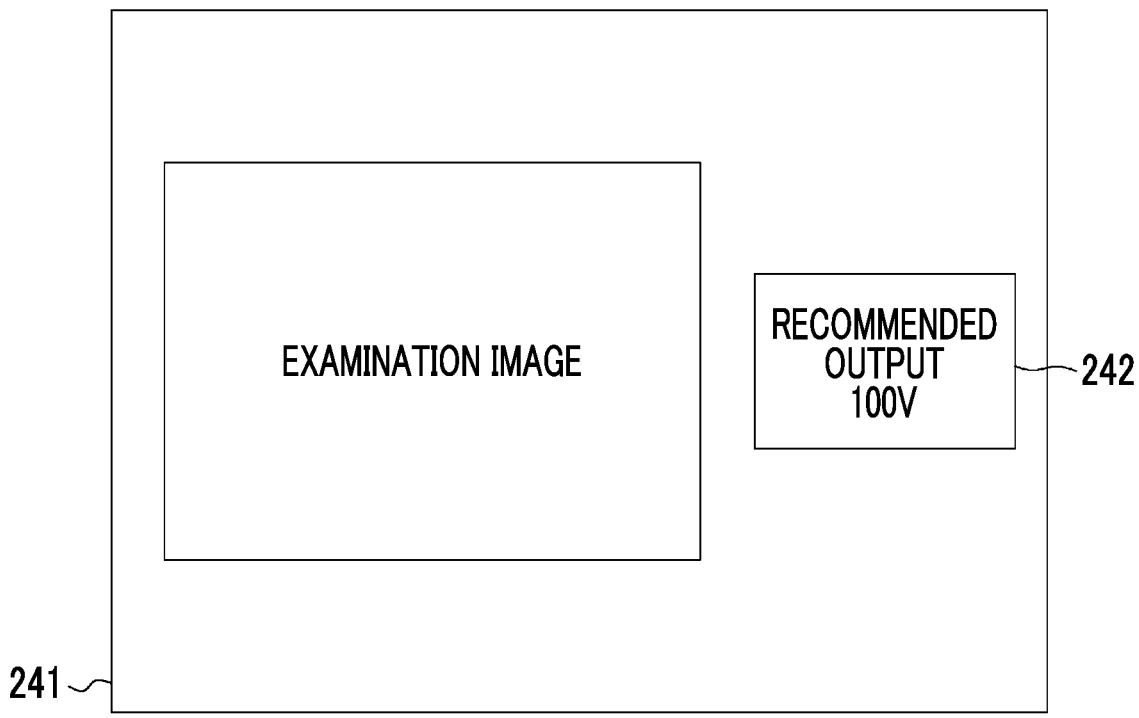
FIG. 29 is an image diagram showing an example of an incision support information screen.

FIG. 28 shows signals transmitted and received by the incision support information generation unit 240. The incision suitable site information, the incision unsuitable site information, and/or the suitability output by the classifier 110 are transmitted to the incision support information generation unit 240 (also refer to FIG. 2). The incision support information generation unit 240 generates incision support information on the basis of the incision suitable site information, the incision unsuitable site information, and the suitability. The incision support information is, for example, information regarding a treatment tool suitable for an examination image, information regarding an angle and a recommended angle of the treatment tool with an acceleration sensor, and information regarding a recommended output of the treatment tool. The incision support information is transmitted to the display control unit 200, and is displayed on the display 17 as a incision support information screen 241 together with the examination image. FIG. 29 shows an example of the incision support information screen 241, in which it is displayed that a recommended output 242 of the treatment tool is 100V. It is preferable that the incision support information is associated with the examination image to be used as a learning image, and the classifier 110 learns the learning image. With the above configuration, it is possible to present information regarding a treatment tool for safely performing incision to an operator.

In the present embodiment, the example in which the medical image processing device 11 is connected to the endoscope system 10 has been described, but the present invention is not limited to this, and other medical devices may be used. As the endoscope 12, a rigid scope or a flexible scope may be used. In the endoscope system 10, a part or the whole of the examination image acquisition unit 60 and/or the first central control unit 55 may be provided in an image processing device that communicates with, for example, the processor device 15 and cooperates with the endoscope system 10. For example, a part or the whole of the examination image acquisition unit 60 and/or the first central control unit 55 may be provided in a diagnostic support device that acquires an image picked up by the endoscope 12 directly from the endoscope system 10 or indirectly from a PACS. A part or the whole of the examination image acquisition unit 60 and/or the first central control unit 55 of the endoscope system 10 may be provided in a medical service support device including the endoscope system 10 and connected to various examination devices such as a first examination device, a second examination device, . . . , and an N-th examination device via a network.

In the present embodiment, hardware structures of processing units executing various processes, such as the image acquisition unit 50, the DSP 52, the noise reduction unit 53, the image processing switching unit 54, the examination image acquisition unit 60, the image input unit 100, the classifier 110, the display image generation unit 150, the display control unit 200, and the notification control unit 210 are various processors as described below. The various processors include a programmable logic device (PLD), which is a processor of which a circuit configuration can be changed after manufacturing, such as a central processing unit (CPU) or a field programmable gate array (FPGA) that is a general-purpose processor that executes software (programs) and functions as various processing units, a dedicated electric circuit that is a processor having a circuit configuration specially designed to execute various processes, and the like.

One processing unit may be configured with one of these various processors, or may be configured with a combination of two or more processors of the same type or different types (for example, a plurality of FPGAs or a combination of a CPU and an FPGA). A plurality of processing units may be configured by one processor. As an example of configuring a plurality of processing units with one processor, first, there is a form in which one processor is configured by a combination of one or more CPUs and software, as typified by a computer used for a client or a server, and this processor functions as a plurality of processing units. Second, as typified by system on chip (SoC), there is a form in which a processor that realizes functions of the entire system including a plurality of processing units with one integrated circuit (IC) chip is used. As described above, the various processing units are configured by using one or more of the above various processors as a hardware structure.

The hardware structure of these various processors is, more specifically, an electric circuit (circuitry) in which circuit elements such as semiconductor elements are combined. The hardware structure of the storage unit is a storage device such as a hard disk drive (HDD) or a solid state drive (SSD).

EXPLANATION OF REFERENCES

- 10: endoscope system
- 11: medical image processing device
- 12: endoscope
- 12*a*: insertion part
- 12*b*: operating part
- 12*c*: bending part
- 12*d*: tip part
- 12*e*: angle knob
- 12*f*: observation mode selector switch
- 12*g*: image analysis mode selector switch
- 12*h*: still image acquisition instruction switch
- 12*i*: zoom operating part
- 12*j*: forceps port
- 14: light source device
- 15: processor device
- 17: display
- 19: user interface
- 20: light source unit
- 20*a*: V-LED
- 20*b*: B-LED
- 20*c*: G-LED
- 20*d*: R-LED
- 21: light source processor
- 22: optical path coupling portion
- 23: light guide
- 30*a*: Illumination optical system
- 30*b*: image pick-up optical system
- 31: illumination lens
- 41: objective lens
- 42: zoom lens
- 43: image pick-up sensor
- 44: image pick-up processor
- 45: CDS/AGC circuit
- 46: A/D converter
- 50: image acquisition unit
- 52: DSP
- 53: noise reduction unit
- 54: image processing switching unit
- 55: first central control unit
- 60: examination image acquisition unit
- 70: first illumination light image generation unit
- 80: second illumination light image generation unit
- 100: image input unit
- 101: second central control unit
- 110: classifier
- 112: incision suitable site
- 113: display image
- 120, 123, 125, 131, 133, 135, 138, 140, 143: learning image
- 121: muscular layer region
- 122: lesion part
- 124: region where submucosal layer covers muscular layer
- 126, 172, 192: muscular layer
- 127, 173, 193: fibrosis
- 132: submucosal layer without local injection
- 134: submucosal layer with local injection
- 136: submucosal layer into which local injection solution containing indigo carmine is locally injected
- 137, 139, 162, 195: peeling layer
- 141: cautery scar
- 142: coagulated blood
- 144: hood edge
- 150: display image generation unit
- 160: first display image generation unit
- 161: first display image
- 170: second display image generation unit
- 171: second display image
- 181: inter-tissue distance display image
- 182: distance from submucosal layer to muscular layer
- 190: perforation risk image generation unit
- 191: perforation risk image
- 194: submucosal layer
- 200: display control unit
- 210: notification control unit
- 220: sound notification control unit
- 230: notification display control unit
- 231: warning display screen 232: frame
233: warning mark
240: incision support information generation unit
241: incision support information screen
242: recommended output of treatment tool

What is claimed is:

1. A medical image processing device comprising:
a processor configured to:
acquire an examination image of a subject captured by an endoscope;
identify an incision suitable site in the subject included in the examination image;
perform control for outputting incision suitable site information regarding the incision suitable site on the basis of the examination image;
generate, on the basis of the incision suitable site information, a first display image indicating the incision suitable site with a color, a symbol, or a figure;
superimpose the first display image on the examination image; and
output the first display image superimposed on the examination image to a display, wherein
the identification of the incision suitable site information is performed by using a learning image, the learning image being associated with information regarding a position of a muscular layer in the subject, the information regarding the position of the muscular layer in the subject including three-dimensional information indicating a thickness of the submucosal layer covering the surface of the muscular layer and two-dimensional information indicating a range of the muscular layer region in the learning image.

2. The medical image processing device according to claim 1, wherein
the processor is configured to identify an incision unsuitable site in the subject included in the examination image, and perform control for outputting incision unsuitable site information regarding the incision unsuitable site, and
the identification of the incision unsuitable site information is performed by using the learning image additionally associated with a position of fibrosis in the subject.

3. The medical image processing device according to claim 2,
wherein the processor is configured to identify the incision suitable site and the incision unsuitable site by a suitability, and perform control for outputting the incision suitable site information based on the suitability, and
wherein the suitability which becomes higher for a site identified to be able to be more safely incised and lower for a site identified not to be able to be safely incised is a degree of evaluation.

4. The medical image processing device according to claim 3,
wherein the processor is configured to generate a perforation risk image as a heat map in which classifications are color-coded according to the suitability, and perform control for superimposing the perforation risk image on the examination image to be displayed on a display.

5. The medical image processing device according to claim 2, wherein
the processor is configured to generate, on the basis of the incision suitable site information, a second display image indicating the incision unsuitable site with a color, a symbol, or a figure, and perform control for superimposing the second display image on the examination image to be displayed on a display.

6. The medical image processing device according to claim 2, wherein
the processor is configured to perform control for providing a notification with sound or notification display, in a case where the examination image includes the incision unsuitable site.

7. The medical image processing device according to claim 1, wherein
a learning model is generated by using the learning image.

8. The medical image processing device according to claim 1, wherein
the learning image includes the subject into which a local injection solution is locally injected.

9. The medical image processing device according to claim 8, wherein
the local injection solution contains a staining solution.

10. The medical image processing device according to claim 9, wherein
the staining solution is indigo carmine, and
the learning image is associated with a concentration of the indigo carmine.

11. The medical image processing device according to claim 1, wherein
the learning image is associated with presence or absence of a cautery scar and/or coagulated blood in the subject.

12. The medical image processing device according to claim 1, wherein
the learning image is associated with a position of a hood attached to a tip of the endoscope in the subject.

13. The medical image processing device according to claim 1, wherein
the learning image is associated with a distance from a submucosal layer to the muscular layer and/or a distance from the submucosal layer to a lesion part in the subject.

14. The medical image processing device according to claim 1, wherein
the figure is a line.

15. The medical image processing device according to claim 1, wherein
the processor is configured to perform control for displaying a distance from a submucosal layer to the muscular layer on the first display image.

16. The medical image processing device according to claim 1, wherein
the processor is configured to generate, on the basis of the incision suitable site information, incision support information corresponding to the incision suitable site information, and perform control for superimposing the incision support information on the examination image to be displayed on a display.

17. An operation method for a medical image processing device, comprising:
a step of acquiring an examination image of a subject captured by an endoscope;
a step of identifying an incision suitable site in the subject included in the examination image;
a step of performing control for outputting incision suitable site information regarding the incision suitable site;
a step of generating, on the basis of the incision suitable site information, a first display image indicating the incision suitable site with a color, a symbol, or a figure;

a step of superimposing the first display image on the examination image; and a step of outputting the first display image superimposed on the examination image to a display, wherein the identification of the incision suitable site information is performed by using a learning image, the learning image being associated with information regarding a position of a muscular layer in the subject, the information regarding the position of the muscular layer in the subject including three-dimensional information indicating a thickness of the submucosal layer covering the surface of the muscular layer and two-dimensional information indicating a range of the muscular layer region in the learning image.

18. An endoscope system comprising:

the medical image processing device according to claim 1; and the endoscope.

* * * * *